(12) United States Patent
Dietrich et al.

(10) Patent No.: US 9,670,546 B2
(45) Date of Patent: Jun. 6, 2017

(54) METHODS AND NUCLEIC ACIDS FOR ANALYSES OF CELL PROLIFERATIVE DISORDERS

(75) Inventors: Dimo Dietrich, Berlin (DE); Ralf Lesche, Berlin (DE); Anne Fassbender, Berlin (DE); Manuel Krispin, Berlin (DE); Joern Dietrich, Berlin (DE)

(73) Assignee: EPIGENOMICS AG, Berlin (DE)

( * ) Notice: Subject to any disclaimer, the term of this patent is extended or adjusted under 35 U.S.C. 154(b) by 0 days.

(21) Appl. No.: 13/002,502

(22) PCT Filed: Jul. 15, 2009

(86) PCT No.: PCT/EP2009/059034
§ 371 (c)(1),
(2), (4) Date: Feb. 1, 2011

(87) PCT Pub. No.: WO2010/007083
PCT Pub. Date: Jan. 21, 2010

(65) Prior Publication Data
US 2011/0160091 A1    Jun. 30, 2011

(30) Foreign Application Priority Data
Jul. 15, 2008 (EP) .................................... 08160382

(51) Int. Cl.
C12P 21/00 (2006.01)
C12Q 1/68 (2006.01)

(52) U.S. Cl.
CPC ..... *C12Q 1/6886* (2013.01); *C12Q 2600/106* (2013.01); *C12Q 2600/112* (2013.01); *C12Q 2600/118* (2013.01); *C12Q 2600/136* (2013.01); *C12Q 2600/154* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| 6,200,756 B1 | 3/2001 | Herman |
| 2005/0100933 A1 | 5/2005 | Erlander et al. |
| 2007/0264659 A1* | 11/2007 | An et al. ............................ 435/6 |
| 2007/0269823 A1* | 11/2007 | Huehn et al. ..................... 435/6 |

FOREIGN PATENT DOCUMENTS

| WO | WO 99/28498 A2 | 6/1999 |
| WO | WO 01/81622 A2 | 11/2001 |
| WO | WO 2005/100606 A2 | 10/2005 |
| WO | WO 2007/010258 A2 | 1/2007 |
| WO | WO 2007/085497 A2 | 8/2007 |

OTHER PUBLICATIONS

Ehrlich et al. (2002 Oncogene vol. 21 p. 5400-5413).*
Cottrell (Clinical Biochemistry 2004 vol. 37 p. 595-604).*
Walsh et al. (Genes & Development (1999) vol. 13, pp. 26-34).*
Booken et al., "Sézary Syndrome is a Unique Cutaneous T-Cell Lymphoma as Identified by an Expanded Gene Signature Including Diagnostic Marker Molecules CDO1 and DNM3," *Leukemia* (2008), 22:393-399, Nature Publishing Group.
Booken et al., "Sézary Syndrome is a Unique Cutaneous T-Cell Lymphoma as Identified by an Expanded Gene Signature Including Diagnostic Marker Molecules CDO1 and DNM3," *Leukemia* (2008), 22:393-399, Supplemental Data, Nature Publishing Group.
Hess et al., "Pharmacogenomic Predictor of Sensitivity to Preoperative Chemotherapy with Paclitaxel and Fluorouracil, Doxorubicin, and Cyclophosphamide in Breast Cancer," *J. Clin. Oncol.* (2006), 24(26):4236-4244, American Society of Clinical Oncology.
Li et al., "Integrated Gene Expression Profile Predicts Prognosis of Breast Cancer Patients," *Breast Cancer Res.* (2009), 113:231-237, Springer Science+Business Media, LLC.
Wang et al., "Comparison of the Time Courses of Selective Gene Expression and Dopaminergic Depletion Induced by MPP+ in MN9D Cells," *Neurochem. Int.* (2008) 52:1037-1043, Elsevier Ltd.
Jones P A: "The DNA methylation paradox", Trends in Genetics, Elsevier Science Publishers B.V. Amsterdam, NL, vol. 15, No. 1, Jan. 1, 1999 (Jan. 1, 1999), pp. 34-37, XP004155549.
European Office Action from application No. 09 780 607.9 (Jun. 14, 2013).
International Search Report with Written Opinion corresponding to International Patent Application No. PCT/EP2009/059034, mailed Jan. 7, 2010.

* cited by examiner

*Primary Examiner* — Celine Qian
(74) *Attorney, Agent, or Firm* — Lathrop & Gage, LLP; James H. Velema, Esq.; Sean M. Coughlin, Esq.

(57) ABSTRACT

The invention provides methods, nucleic acids and kits for determining the prognosis of a subject having cell proliferative disorder, preferably cancer. The invention discloses genomic sequences the methylation patterns of which have utility for the improved detection of said disorder, thereby enabling the improved diagnosis and treatment of patients.

5 Claims, 2 Drawing Sheets

METHODS AND NUCLEIC ACIDS FOR ANALYSES OF CELL PROLIFERATIVE DISORDERS

CROSS REFERENCE TO RELATED APPLICATIONS

This application is a 35 USC §371 National Stage application of International Application No. PCT/EP2009/059034 filed Jul. 15, 2009, now pending; which claims the benefit under 35 USC §119(a) to EP Patent Application No. 08160382.1 filed Jul. 15, 2008. The disclosure of each of the prior applications is considered part of and is incorporated by reference in the disclosure of this application.

FIELD OF THE INVENTION

The present invention relates to genomic DNA markers useful in determining the prognosis of a subject having cell proliferative disorder, preferably cancer. Particular embodiments provide methods, nucleic acids, nucleic acid arrays and kits useful for determining the prognosis of a subject having a cell proliferative disorder.

BACKGROUND

Anthracyclines are a large group of compounds synthesized by different *Streptomyces* species. They possess antibiotic activity and have cytotoxic effects on eukaryotic cells. All anthracyclines have a tetrahydronaphthacenedione ring structure attached by a glycosidic linkage to a sugar molecule, structural diversity of anthracyclines is generated by modifications of the backbone including a large number of different side chains.

Anthracyclines have excellent antineoplastic activity in metastatic, neoadjuvant, and adjuvant settings and are used in the treatment of various haematopoietic and solid tumours. Commonly used anthracyclines include but are not limited to mitoxantrone, doxorubicin, aclarubicin, daunorubicin, epirubicin and idarubicin. Although their mechanism of chemotherapeutic action is unclear involves noncovalent DNA intercalation, formation of covalent DNA adducts, topoisomerase II (topo II) poisoning, and free radical effects on cellular membranes and DNA. However, the clinical utility of anthracyclines are limited due to acute and chronic toxicities, particularly cardiotoxicity, myelosuppression, nausea and vomiting, and alopecia.

Heart failure following anthracycline therapy is a major clinical problem in cancer treatment. The establishment of predictors of the anthracycline treatment outcome would allow the identification and exclusion of individuals who would not benefit from said treatment, and thus to increase the safety of anthracycline treatment. Furthermore by determining which patients would benefit from Anthracycline treatment, but wherein said predicted outcome is suboptimal patients can be recommended for further chemotherapeutic or other treatments. Conversely by determining which patients would be adequately treated by anthracycline treatment alone the over-treatment of patients can be prevented.

SUMMARY OF THE INVENTION

The present invention provides a method for determining the prognosis of a subject having cell proliferative disorder, preferably cancer, in a subject comprising determining the expression levels of at least one gene selected from the group consisting of CDO1; APC; BMPR1A; CTAGE5; CXCL12; NCR1; NFATC2; PAX9; POU4F3; ZBTB16 in a biological sample isolated from said subject wherein methylation and/or expression status is indicative of the prognosis of said subject. Said method is particularly suited to determining prognosis of said subject subsequent to a therapy comprising at least one anthracycline. Various aspects of the present invention provide genetic markers, whereby expression analysis of said marker enables the determination of the prognosis of a subject having cell proliferative disorder, preferably cancer. The method according to the invention may be used for the analysis of a wide variety of cell proliferative disorders suitable for treatment with anthracyclines including, but not limited to, breast cancer, ovarian cancer, transitional cell bladder cancer, bronchogenic lung cancer, thyroid cancer, pancreatic cancer, prostate cancer, uterine cancer, testicular cancer, gastric cancer, soft tissue and osteogenic sarcomas, neuroblastoma, Wilms' tumor, malignant lymphoma (Hodgkin's and non-Hodgkin's), acute myeloblastic leukemia, acute lymphoblastic leukemia, Kaposi's sarcoma, Ewing's tumor, refractory multiple myeloma, squamous cell carcinomas of the head, neck, cervix, and vagina.

The method according to the invention may be used to provide a prediction of patient survival and/or relapse following treatment by means of a therapy comprising at least one anthracycline.

In one embodiment the invention provides a method for determining the prognosis of said subject comprising determining the expression levels of at least one gene selected from the group consisting of CDO1; APC; BMPR1A; CTAGE5; CXCL12; NCR1; NFATC2; PAX9; POU4F3; ZBTB16 in a biological sample isolated from said subject wherein under-expression and/or CpG methylation is indicative of the prognosis of said subject. In one embodiment said prognosis is the subject's prognosis subsequent to a therapy comprising at least one anthracycline. In one embodiment said expression level is determined by detecting the presence, absence or level of mRNA transcribed from said gene. In a further embodiment said expression level is determined by detecting the presence, absence or level of a polypeptide encoded by said gene or sequence thereof.

In a further preferred embodiment said expression is determined by detecting the presence, absence or amount of CpG methylation within said gene, and there from deducing the pronosis of said subject having cell proliferative disorder, preferably cancer.

Said method comprises the following steps: i) contacting genomic DNA isolated from a biological sample (preferably selected from the group consisting of cell lines, histological slides, paraffin embedded tissues, biopsies, tissue embedded in paraffin, bodily fluids (such as but not limited to nipple aspirate and blood) and all possible combinations thereof) obtained from the subject with at least one reagent, or series of reagents that distinguishes between methyllated and non-methylated CpG dinucleotides within at least one target region of the genomic DNA, wherein the nucleotide sequence of said target region comprises at least one CpG dinucleotide sequence of at least one gene selected from the group consisting of CDO1; APC; BMPR1A; CTAGE5; CXCL12; NCR1; NFATC2; PAX9; POU4F3; and ZBTB16 and ii) determining the prognosis of a subject having cell proliferative disorder, preferably cancer. Preferably the target region comprises, or hybridizes under stringent conditions to a sequence of at least 16 contiguous nucleotides of SEQ ID NO: 1-10, or preferred regions thereof according to SEQ ID NO: 11-20. In one embodiment said prognosis is the subject's prognosis subsequent to a therapy comprising at least one anthracycline.

Said use of the gene may be enabled by means of any analysis of the expression of the gene, by means of mRNA expression analysis or protein expression analysis. However, in the most preferred embodiment of the invention the determination of the prognosis of a subject having cell proliferative disorder, preferably cancer, is enabled by means of analysis of the methylation status of at least one gene selected from the group consisting of CDO1; APC; BMPR1A; CTAGE5; CXCL12; NCR1; NFATC2; PAX9; POU4F3; and ZBTB16, and/or promoter or regulatory elements thereof.

The invention provides a method for the analysis of biological samples for features associated with the progression of cell proliferative disorder, preferably cancer, the method characterized in that the nucleic acid, or a fragment thereof of SEQ ID NO: 1-10, or preferred regions thereof according to SEQ ID NO: 11-20 is contacted with a reagent or series of reagents capable of distinguishing between methylated and non methylated CpG dinucleotides within the genomic sequence.

The present invention provides a method for ascertaining epigenetic parameters of genomic DNA associated with the development of cell proliferative disorder, preferably cancer.

Preferably, the source of the test sample is selected from the group consisting of cell lines, histological slides, paraffin embedded tissues, biopsies, tissue embedded in paraffin, bodily fluids (such as but not limited to nipple aspirate and blood) and all possible combinations thereof and combinations thereof.

Specifically, the present invention provides a method for determining the prognosis of a subject having cell proliferative disorder, preferably cancer suitable for use as a prognostic and/or predictive tool, comprising: obtaining a biological sample comprising genomic nucleic acid(s); contacting the nucleic acid(s), or a fragment thereof, with a reagent or a plurality of reagents sufficient for distinguishing between methylated and non methylated CpG dinucleotide sequences within a target sequence of the subject nucleic acid, wherein the target sequence comprises, or hybridises under stringent conditions to, a sequence comprising at least 16 contiguous nucleotides of SEQ ID NO: 1-10, or preferred regions thereof according to SEQ ID NO: 11-20 said contiguous nucleotides comprising at least one CpG dinucleotide sequence; and determining, based at least in part on said distinguishing, the methylation state of at least one target CpG dinucleotide sequence, or an average, or a value reflecting an average methylation state of a plurality of target CpG dinucleotide sequences. In a preferred embodiment said prognosis is the subject's prognosis subsequent to a therapy comprising at least one anthracycline.

Preferably, distinguishing between methylated and non methylated CpG dinucleotide sequences within the target sequence comprises methylation state-dependent conversion or non-conversion of at least one such CpG dinucleotide sequence to the corresponding converted or non-converted dinucleotide sequence within a sequence selected from the group consisting of SEQ ID NO: 21-40 and 61-80 or preferred regions thereof according to SEQ ID NO: 41-60 and 81-100, and contiguous regions thereof corresponding to the target sequence.

Additional embodiments provide a method for the determination of the prognosis of a subject having cell proliferative disorder, preferably cancer comprising: obtaining a biological sample having subject genomic DNA; extracting the genomic DNA; treating the genomic DNA, or a fragment thereof, with one or more reagents to convert 5-position unmethylated cytosine bases to uracil or to another base that is detectably dissimilar to cytosine in terms of hybridization properties; contacting the treated genomic DNA, or the treated fragment thereof, with an amplification enzyme and at least two primers comprising, in each case a contiguous sequence at least 9 nucleotides in length that is complementary to, or hybridizes under moderately stringent or stringent conditions to a sequence selected from the group consisting SEQ ID NO: 21-40 and 61-80 or preferred regions thereof according to SEQ ID NO: 41-60 and 81-100, and complements thereof, wherein the treated DNA or the fragment thereof is either amplified to produce an amplificate, or is not amplified; and determining, based on a presence, absence or class of, or on a property of said amplificate, the methylation state or an average, or a value reflecting an average of the methylation level of at least one, but more preferably a plurality of CpG dinucleotides of SEQ ID NO: 1-10, or preferred regions thereof according to SEQ ID NO: 11-20.

Preferably, determining comprises use of at least one method selected from the group consisting of: i) hybridizing at least one nucleic acid molecule comprising a contiguous sequence at least 9 nucleotides in length that is complementary to, or hybridizes under moderately stringent or stringent conditions to a sequence selected from the group consisting of SEQ ID NO: 21-40 and 61-80 or preferred regions thereof according to SEQ ID NO: 41-60 and 81-100, and complements thereof; ii) hybridizing at least one nucleic acid molecule, bound to a solid phase, comprising a contiguous sequence at least 9 nucleotides in length that is complementary to, or hybridizes under moderately stringent or stringent conditions to a sequence selected from the group consisting of SEQ ID NO: 21-40 and 61-80 or preferred regions thereof according to SEQ ID NO: 41-60 and 81-100, and complements thereof; iii) hybridizing at least one nucleic acid molecule comprising a contiguous sequence at least 9 nucleotides in length that is complementary to, or hybridizes under moderately stringent or stringent conditions to a sequence selected from the group consisting of SEQ ID NO: 21-40 and 61-80 or preferred regions thereof according to SEQ ID NO: 41-60 and 81-100, and complements thereof, and extending at least one such hybridized nucleic acid molecule by at least one nucleotide base; and iv) sequencing of the amplificate.

Further embodiments provide a method for the analysis (i.e. determining disease progression and/or patient prognosis) of a cell proliferative disorder, preferably cancer, comprising: obtaining a biological sample having subject genomic DNA; extracting the genomic DNA; contacting the genomic DNA, or a fragment thereof, comprising one or more sequences selected from the group consisting of SEQ ID NO: 1-10, or preferred regions thereof according to SEQ ID NO: 11-20 or a sequence that hybridizes under stringent conditions thereto, with one or more methylation-sensitive restriction enzymes, wherein the genomic DNA is either digested thereby to produce digestion fragments, or is not digested thereby; and determining, based on a presence, absence or class of, or on property of at least one such fragment, the methyllation state of at least one CpG dinucleotide sequence of SEQ ID NO: 1-10, or preferred regions thereof according to SEQ ID NO: 11-20 or an average, or a value reflecting an average methylation state of a plurality of CpG dinucleotide sequences thereof. Preferably, the digested or undigested genomic DNA is amplified prior to said determining.

Additional embodiments provide novel genomic and chemically modified nucleic acid sequences, as well as oligonucleotides and/or PNA-oligomers for analysis of cytosine methylation patterns within SEQ ID NO: 1-10, or preferred regions thereof according to SEQ ID NO: 11-20.

DETAILED DESCRIPTION OF THE INVENTION

Definitions:

The term "prognosis" as used herein refers to a forecast of the course of a disease that is to be expected without the application of any treatment or intervention, whereas said course of disease includes the likelihood of progression of the disease, in particular its aggressiveness and metastatic potential in case the disease is a malignant tumor.

The term "prediction" as used herein refers to the likelihood of a patient suffering from a disease to respond to a treatment or an intervention directed against said disease. Thereby, said response is preferably defined according to patient survival. The term "prediction" is preferably used to define patients with high, low and intermediate length of survival or recurrence after treatment.

The term "Observed/Expected Ratio" ("O/E Ratio") refers to the frequency of CpG dinucleotides within a particular DNA sequence, and corresponds to the [number of CpG sites/(number of C bases×number of G bases)]/band length for each fragment.

The term "CpG island" refers to a contiguous region of genomic DNA that satisfies the criteria of (1) having a frequency of CpG dinucleotides corresponding to an "Observed/Expected Ratio">0.6, and (2) having a "GC Content">0.5. CpG islands are typically, but not always, between about 0.2 to about 1 KB, or to about 2 kb in length.

The term "methylation state" or "methylation status" refers to the presence, absence or class of 5-methylcytosine ("5-mCyt") at one or a plurality of CpG dinucleotides within a DNA sequence. Methylation states at one or more particular CpG methylation sites (each having two CpG dinucleotide sequences) within a DNA sequence include "unmethylated," "fullymethylated" and "hemi-methylated."

The term "hemi-methylation" or "hemimethylation" refers to the methylation state of a double stranded DNA wherein only one strand thereof is methylated.

The term 'AUC' as used herein is an abbreviation for the area under a curve. In particular it refers to the area under a Receiver Operating Characteristic (ROC) curve. The ROC curve is a plot of the true positive rate against the false positive rate for the different possible cut points of a diagnostic test. It shows the trade-off between sensitivity and specificity depending on the selected cut point (any increase in sensitivity will be accompanied by a decrease in specificity). The area under an ROC curve (AUC) is a measure for the accuracy of a test (the larger the area the better, optimum is 1, a random test would have a ROC curve lying on the diagonal with an area of 0.5; for reference: J. P. Egan. Signal Detection Theory and ROC Analysis, Academic Press, New York, 1975).

The term "microarray" refers broadly to both "DNA microarrays," and 'DNA chip(s),' as recognized in the art, encompasses all art-recognized solid supports, and encompasses all methods for affixing nucleic acid molecules thereto or synthesis of nucleic acids thereon.

"Genetic parameters" are mutations and polymorphisms of genes and sequences further required for their regulation. To be designated as mutations are, in particular, insertions, deletions, point mutations, inversions and polymorphisms and, particularly preferred, SNPs (single nucleotide polymorphisms).

"Epigenetic parameters" are, in particular, cytosine methylation. Further epigenetic parameters include, for example, the acetylation of histones which, however, cannot be directly analyzed using the described method but which, in turn, correlate with the DNA methylation.

The term "bisulfite reagent" refers to a reagent comprising bisulfite, disulfite, hydrogen sulfite or combinations thereof, useful as disclosed herein to distinguish between methylated and unmethylated CpG dinucleotide sequences.

The term "Methylation assay" refers to any assay for determining the methylation state of one or more CpG dinucleotide sequences within a sequence of DNA.

The term "MS.AP-PCR" (Methylation-Sensitive Arbitrarily-Primed Polymerase Chain Reaction) refers to the art-recognized technology that allows for a global scan of the genome using CG-rich primers to focus on the regions most likely to contain CpG dinucleotides, and described by Gonzalgo et al., *Cancer Research* 57:594-599, 1997.

The term "MethyLight™" refers to the art-recognized fluorescence-based real-time PCR technique described by Eads et al., *Cancer Res.* 59:2302-2306, 1999.

The term "HeavyMethyl™" assay, in the embodiment thereof implemented herein, refers to an assay, wherein methylation specific blocking probes (also referred to herein as blockers) covering CpG positions between, or covered by the amplification primers enable methylation-specific selective amplification of a nucleic acid sample.

The term "HeavyMethyl™ MethyLight™" assay, in the embodiment thereof implemented herein, refers to a HeavyMethyl™ MethyLight™ assay, which is a variation of the MethyLight™ assay, wherein the MethyLight™ assay is combined with methylation specific blocking probes covering CpG positions between the amplification primers.

The term "Ms-SNuPE" (Methylation-sensitive Single Nucleotide Primer Extension) refers to the art-recognized assay described by Gonzalgo and Jones, *Nucleic Acids Res.* 25:2529-2531, 1997.

The term "MSP" (Methylation-specific PCR) refers to the art-recognized methylation assay described by Herman et al. *Proc. Natl. Acad. Sci. USA* 93:9821-9826, 1996, and by U.S. Pat. No. 5,786,146.

The term "COBRA" (Combined Bisulfite Restriction Analysis) refers to the art-recognized methylation assay described by Xiong and Laird, *Nucleic Acids Res.* 25:2532-2534, 1997.

The term "MCA" (Methylated CpG Island Amplification) refers to the methylation assay described by Toyota et al., *Cancer Res.* 59:2307-12, 1999, and in WO 00/26401.

The term "hybridization" is to be understood as a bond of an oligonucleotide to a complementary sequence along the lines of the Watson-Crick base pairings in the sample DNA, forming a duplex structure.

"Stringent hybridization conditions," as defined herein, involve hybridizing at 68° C. in 5×SSC/5×Denhardt's solution/1.0% SDS, and washing in 0.2×SSC/0.1% SDS at room temperature, or involve the art-recognized equivalent thereof (e.g., conditions in which a hybridization is carried out at 60° C. in 2.5×SSC buffer, followed by several washing steps at 37° C. in a low buffer concentration, and remains stable). Moderately stringent conditions, as defined herein, involve including washing in 3×SSC at 42° C., or the art-recognized equivalent thereof. The parameters of salt concentration and temperature can be varied to achieve the optimal level of identity between the probe and the target nucleic acid. Guidance regarding such conditions is available in the art, for example, by Sambrook et al., 1989, Molecular Cloning, A Laboratory Manual, Cold Spring Harbor Press, N.Y.; and Ausubel et al. (eds.), 1995, Current Protocols in Molecular Biology, (John Wiley and Sons, N.Y.) at Unit 2.10.

The terms "Methylation-specific restriction enzymes" or "methylation-sensitive restriction enzymes" shall be taken to mean an enzyme that selectively digests a nucleic acid dependant on the methylation state of its recognition site. In the case of such restriction enzymes which specifically cut if the recognition site is not methylated or hemimethylated, the cut will not take place, or with a significantly reduced efficiency, if the recognition site is methylated. In the case of such restriction enzymes which specifically cut if the recognition site is methyllated, the cut will not take place, or with a significantly reduced efficiency if the recognition site is not methylated. Preferred are methylation-specific restriction enzymes, the recognition sequence of which contains a CG dinucleotide (for instance cgcg or cccggg). Further preferred for some embodiments are restriction enzymes that do not cut if the cytosine in this dinucleotide is methylated at the carbon atom C5.

"Non-methylation-specific restriction enzymes" or "non-methylation-sensitive restriction enzymes" are restriction enzymes that cut a nucleic acid sequence irrespective of the methylation state with nearly identical efficiency. They are also called "methylation-unspecific restriction enzymes."

In reference to composite array sequences, the phrase "contiguous nucleotides" refers to a contiguous sequence region of any individual contiguous sequence of the composite array, but does not include a region of the composite array sequence that includes a "node," as defined herein above.

The term "at least one gene selected from the group consisting of CDO1; APC; BMPR1A; CTAGE5; CXCL12; NCR1; NFATC2; PAX9; POU4F3; and ZBTB16" shall be taken to include all transcript variants thereof and all promoter and regulatory elements thereof. Furthermore as a plurality of SNPs are known within said gene the term shall be taken to include all sequence variants thereof.

Overview:

The present invention provides a method for determining the prognosis of a subject having cell proliferative disorder, preferably cancer comprising determining the methylation and/or expression levels of at least one gene selected from the group consisting of CDO1; APC; BMPR1A; CTAGE5; CXCL12; NCR1; NFATC2; PAX9; POU4F3; and ZBTB16 in a biological sample isolated from said subject wherein methylation and/or expression status is indicative of the prognosis of said subject having cell proliferative disorder, preferably cancer. In one embodiment said prognosis is the subject's prognosis subsequent to a therapy comprising at least one anthracycline.

In addition to the embodiments above wherein the methylation analysis of at least one gene selected from the group consisting of CDO1; APC; BMPR1A; CTAGE5; CXCL12; NCR1; NFATC2; PAX9; POU4F3; and ZBTB16 is analysed, the invention presents further panels of genes comprising at least one gene selected from the group consisting of CDO1; APC; BMPR1A; CTAGE5; CXCL12; NCR1; NFATC2; PAX9; POU4F3; and ZBTB16 with novel utility for the determination of the prognosis of a subject having cell proliferative disorder, preferably cancer.

Bisulfite modification of DNA is an art-recognized tool used to assess CpG methylation status. The most frequently used method for analyzing DNA for the presence of 5-methylcytosine is based upon the reaction of bisulfite with cytosine whereby, upon subsequent alkaline hydrolysis, cytosine is converted to uracil which corresponds to thymine in its base pairing behavior. Significantly, however, 5-methylcytosine remains unmodified under these conditions. Consequently, the original DNA is converted in such a manner that methylcytosine, which originally could not be distinguished from cytosine by its hybridization behavior, can now be detected as the only remaining cytosine using standard, art-recognized molecular biological techniques, for example, by amplification and hybridization, or by sequencing. All of these techniques are based on differential base pairing properties, which can now be fully exploited.

An overview of art-recognized methods for detecting 5-methylcytosine is provided by Rein, T., et al., *Nucleic Acids Res.*, 26:2255, 1998.

The bisulfite technique, barring few exceptions (e.g., Zeschnigk M, et al., *Eur J Hum Genet.* 5:94-98, 1997), is currently only used in research. In general, short, specific fragments of a known gene are amplified subsequent to a bisulfite treatment, and either completely sequenced (Olek and Walter, *Nat. Genet.* 1997 17:275-6, 1997), subjected to one or more primer extension reactions (Gonzalgo and Jones, Nucleic Acids Res., 25:2529-31, 1997; WO 95/00669; U.S. Pat. No. 6,251,594) to analyse individual cytosine positions, or treated by enzymatic digestion (Xiong and Laird, *Nucleic Acids Res.*, 25:2532-4, 1997). Detection by hybridisation has also been described in the art (Olek et al., WO 99/28498). Additionally, use of the bisulfite technique for methylation detection with respect to individual genes has been described (Grigg and Clark, *Bioessays,* 16:431-6, 1994; Zeschnigk M, et al., Hum Mol. Genet., 6:387-95, 1997; Feil R, et al., *Nucleic Acids Res.,* 22:695-, 1994; Martin V, et al., Gene, 157:261-4, 1995; WO 97/46705 and WO 95/15373).

The present invention provides for the use of the bisulfite technique, in combination with one or more methylation assays, for determination of the methylation status of CpG dinucleotide sequences within SEQ ID NO: 1-10, or preferred regions thereof according to SEQ ID NO: 11-20. Genomic CpG dinucleotides can be methylated or unmethylated (alternatively known as up- and down-methylated respectively). However the methods of the present invention are suitable for the analysis of biological samples of a heterogeneous nature e.g. a low concentration of tumor cells within a background of blood or ejaculate. Accordingly, when analyzing the methylation status of a CpG position within such a sample the person skilled in the art may use a quantitative assay for determining the level (e.g. percent, fraction, ratio, proportion or degree) of methylation at a particular CpG position as opposed to a methylation state. Accordingly the term methylation status or methylation state should also be taken to mean a value reflecting the degree of methylation at a CpG position. Unless specifically stated the terms "hypermethylated" or "upmethylated" shall be taken to mean a methylation level above that of a specified cut-off point, wherein said cut-off may be a value representing the average or median methylation level for a given population, or is preferably an optimized cut-off level. The "cut-off" is also referred herein as a "threshold". In the context of the present invention the terms "methylated", "hypermethylated" or "upmethylated" shall be taken to include a methylation level above the cut-off be zero (0) % (or equivalents thereof) methylation for all CpG positions within and associated with (e.g. in promoter or regulatory regions) at least one gene selected from the group consisting of CDO1; APC; BMPR1A; CTAGE5; CXCL12; NCR1; NFATC2; PAX9; POU4F3; and ZBTB16.

According to the present invention, determination of the methylation status of CpG dinucleotide sequences within SEQ ID NO: 1-10, or preferred regions thereof according to SEQ ID NO: 11-20 have utility in the determination of the prognosis of a subject having cell proliferative disorder, preferably cancer.

Methylation Assay Procedures. Various methylation assay procedures are known in the art, and can be used in conjunction with the present invention. These assays allow for determination of the methylation state of one or a plurality of CpG dinucleotides (e.g., CpG islands) within a DNA sequence. Such assays involve, among other techniques, DNA sequencing of bisulfite-treated DNA, PCR (for sequence-specific amplification), Southern blot analysis, and use of methylation-sensitive restriction enzymes.

For example, genomic sequencing has been simplified for analysis of DNA methylation patterns and 5-methylcytosine distribution by using bisulfite treatment (Frommer et al., *Proc. Natl. Acad. Sci. USA* 89:1827-1831, 1992). Additionally, restriction enzyme digestion of PCR products amplified from bisulfite-converted DNA is used, e.g., the method described by Sadri and Hornsby (*Nucl. Acids Res.* 24:5058-5059, 1996), or COBRA (Combined Bisulfite Restriction Analysis) (Xiong and Laird, *Nucleic Acids Res.* 25:2532-2534, 1997).

COBRA. COBRA™ analysis is a quantitative methylation assay useful for determining DNA methylation levels at specific gene loci in small amounts of genomic DNA (Xiong and Laird, *Nucleic Acids Res.* 25:2532-2534, 1997). Briefly, restriction enzyme digestion is used to reveal methylation-dependent sequence differences in PCR products of sodium bisulfite-treated DNA. Methylation-dependent sequence differences are first introduced into the genomic DNA by standard bisulfite treatment according to the procedure described by Frommer et al. (*Proc. Natl. Acad. Sci. USA* 89:1827-1831, 1992). PCR amplification of the bisulfite converted DNA is then performed using primers specific for the CpG islands of interest, followed by restriction endonuclease digestion, gel electrophoresis, and detection using specific, labeled hybridization probes. Methylation levels in the original DNA sample are represented by the relative amounts of digested and undigested PCR product in a linearly quantitative fashion across a wide spectrum of DNA methylation levels. In addition, this technique can be reliably applied to DNA obtained from micro-dissected paraffin-embedded tissue samples.

Typical reagents (e.g., as might be found in a typical COBRA™-based kit) for COBRA™ analysis may include, but are not limited to: PCR primers for specific gene (or bisulfite treated DNA sequence or CpG island); restriction enzyme and appropriate buffer; gene-hybridization oligonucleotide; control hybridization oligonucleotide; kinase labeling kit for oligonucleotide probe; and labeled nucleotides. Additionally, bisulfite conversion reagents may include: DNA denaturation buffer; sulfonation buffer; DNA recovery reagents or kits (e.g., precipitation, ultrafiltration, affinity column); desulfonation buffer; and DNA recovery components.

Preferably, assays such as "MethyLight™" (a fluorescence-based real-time PCR technique) (Eads et al., *Cancer Res.* 59:2302-2306, 1999), Ms-SNuPE™ (Methylation-sensitive Single Nucleotide Primer Extension) reactions (Gonzalgo and Jones, *Nucleic Acids Res.* 25:2529-2531, 1997), methylation-specific PCR ("MSP"; Herman et al., *Proc. Natl. Acad. Sci. USA* 93:9821-9826, 1996; U.S. Pat. No. 5,786,146), and methylated CpG island amplification ("MCA"; Toyota et al., *Cancer Res.* 59:2307-12, 1999) are used alone or in combination with other of these methods.

The "HeavyMethyl™" assay, technique is a quantitative method for assessing methylation differences based on methylation specific amplification of bisulfite treated DNA. Methylation specific blocking probes (also referred to herein as blockers) covering CpG positions between, or covered by the amplification primers enable methylation-specific selective amplification of a nucleic acid sample.

The term "HeavyMethyl™ MethyLight™" assay, in the embodiment thereof implemented herein, refers to a HeavyMethyl™ MethyLight™ assay, which is a variation of the MethyLight™ assay, wherein the MethyLight™ assay is combined with methylation specific blocking probes covering CpG positions between the amplification primers. The HeavyMethyl™ assay may also be used in combination with methylation specific amplification primers.

Typical reagents (e.g., as might be found in a typical MethyLight™-based kit) for HeavyMethyl™ analysis may include, but are not limited to: PCR primers for specific genes (or bisulfite treated DNA sequence or CpG island); blocking oligonucleotides; optimized PCR buffers and deoxynucleotides; and Taq polymerase.

MSP. MSP (methylation-specific PCR) allows for assessing the methylation status of virtually any group of CpG sites within a CpG island, independent of the use of methylation-sensitive restriction enzymes (Herman et al. *Proc. Natl. Acad. Sci. USA* 93:9821-9826, 1996; U.S. Pat. No. 5,786,146). Briefly, DNA is modified by sodium bisulfite converting all unmethylated, but not methylated cytosines to uracil, and subsequently amplified with primers specific for methylated versus unmethylated DNA. MSP requires only small quantities of DNA, is sensitive to 0.1% methylated alleles of a given CpG island locus, and can be performed on DNA extracted from paraffin-embedded samples. Typical reagents (e.g., as might be found in a typical MSP-based kit) for MSP analysis may include, but are not limited to: methylated and unmethylated PCR primers for specific gene (or bisulfite treated DNA sequence or CpG island), optimized PCR buffers and deoxynucleotides, and specific probes.

MethyLight™. The MethyLight™ assay is a high-throughput quantitative methylation assay that utilizes fluorescence-based real-time PCR (TaqMan™) technology that requires no further manipulations after the PCR step (Eads et al., *Cancer Res.* 59:2302-2306, 1999). Briefly, the MethyLight™ process begins with a mixed sample of genomic DNA that is converted, in a sodium bisulfite reaction, to a mixed pool of methylation-dependent sequence differences according to standard procedures (the bisulfite process converts unmethylated cytosine residues to uracil). Fluorescence-based PCR is then performed in a "biased" (with PCR primers that overlap known CpG dinucleotides) reaction. Sequence discrimination can occur both at the level of the amplification process and at the level of the fluorescence detection process.

The MethyLight™ assay may be used as a quantitative test for methylation patterns in the genomic DNA sample, wherein sequence discrimination occurs at the level of probe hybridization. In this quantitative version, the PCR reaction provides for a methylation specific amplification in the presence of a fluorescent probe that overlaps a particular putative methylation site. An unbiased control for the amount of input DNA is provided by a reaction in which neither the primers, nor the probe overlie any CpG dinucleotides. Alternatively, a qualitative test for genomic methylation is achieved by probing of the biased PCR pool with either control oligonucleotides that do not "cover" known methylation sites (a fluorescence-based version of the HeavyMethyl™ and MSP techniques), or with oligonucleotides covering potential methylation sites.

The MethyLight™ process can by used with any suitable probes e.g. "TagMan®", Lightcycler® and the likes. For example, double-stranded genomic DNA is treated with sodium bisulfite and subjected to one of two sets of PCR reactions using TaqMan® probes; e.g., with MSP primers and/or HeavyMethyl blocker oligonucleotides and TaqMan® probe. The TaqMan® probe is dual-labeled with fluorescent "reporter" and "quencher" molecules, and is designed to be specific for a relatively high GC content region so that it melts out at about 10° C. higher temperature in the PCR cycle than the forward or reverse primers. This allows the TaqMan® probe to remain fully hybridized during the PCR annealing/extension step. As the Taq polymerase enzymatically synthesizes a new strand during PCR, it will eventually reach the annealed TaqMan® probe. The Taq polymerase 5' to 3' endonuclease activity will then displace the TagMan® probe by digesting it to release the fluorescent reporter molecule for quantitative detection of its now unquenched signal using a real-time fluorescent detection system.

Typical reagents (e.g., as might be found in a typical MethyLight™-based kit) for MethyLight™ analysis may include, but are not limited to: PCR primers for specific gene (or bisulfite treated DNA sequence or CpG island); TaqMan® or Lightcycler® probes; optimized PCR buffers and deoxynucleotides; and Taq polymerase.

The QM™ (quantitative methylation) assay is an alternative quantitative test for methylation patterns in genomic DNA samples, wherein sequence discrimination occurs at the level of probe hybridization. In this quantitative version, the PCR reaction provides for unbiased amplification in the presence of a fluorescent probe that overlaps a particular putative methylation site. An unbiased control for the amount of input DNA is provided by a reaction in which neither the primers, nor the probe overlie any CpG dinucleotides. Alternatively, a qualitative test for genomic methylation is achieved by probing of the biased PCR pool with either control oligonucleotides that do not "cover" known methylation sites (a fluorescence-based version of the HeavyMethyl™ and MSP techniques), or with oligonucleotides covering potential methylation sites.

The QM™ process can by used with any suitable probes e.g. "TaqMan®", Lightcycler® etc. . . . in the amplification process. For example, double-stranded genomic DNA is treated with sodium bisulfite and subjected to unbiased primers and the TaqMan® probe. The TaqMan® probe is dual-labeled with fluorescent "reporter" and "quencher" molecules, and is designed to be specific for a relatively high GC content region so that it melts out at about 10° C. higher temperature in the PCR cycle than the forward or reverse primers. This allows the TaqMan® probe to remain fully hybridized during the PCR annealing/extension step. As the Taq polymerase enzymatically synthesizes a new strand during PCR, it will eventually reach the annealed Taq Man® probe. The Taq polymerase 5' to 3' endonuclease activity will then displace the TaqMan® probe by digesting it to release the fluorescent reporter molecule for quantitative detection of its now unquenched signal using a real-time fluorescent detection system. Typical reagents (e.g., as might be found in a typical QM™-based kit) for QM™ analysis may include, but are not limited to: PCR primers for specific gene (or bisulfite treated DNA sequence or CpG island); TaqMan® or Lightcycler® probes; optimized PCR buffers and deoxynucleotides; and Taq polymerase.

Ms-SNuPE. The Ms-SNuPE™ technique is a quantitative method for assessing methylation differences at specific CpG sites based on bisulfite treatment of DNA, followed by singlenucleotide primer extension (Gonzalgo and Jones, *Nucleic Acids Res.* 25:2529-2531, 1997). Briefly, genomic DNA is reacted with sodium bisulfite to convert unmethylated cytosine to uracil while leaving 5-methylcytosine unchanged. Amplification of the desired target sequence is then performed using PCR primers specific for bisulfite-converted DNA, and the resulting product is isolated and used as a template for methylation analysis at the CpG site(s) of interest. Small amounts of DNA can be analyzed (e.g., micro-dissected pathology sections), and it avoids utilization of restriction enzymes for determining the methylation status at CpG sites.

Typical reagents (e.g., as might be found in a typical Ms-SNuPE™-based kit) for MsSNuPE™ analysis may include, but are not limited to: PCR primers for specific gene (or bisulfite treated DNA sequence or CpG island); optimized PCR buffers and deoxynucleotides; gel extraction kit; positive control primers; Ms-SNuPE™ primers for specific gene; reaction buffer (for the Ms-SNuPE reaction); and labeled nucleotides. Additionally, bisulfite conversion reagents may include: DNA denaturation buffer; sulfonation buffer; DNA recovery regents or kit (e.g., precipitation, ultrafiltration, affinity column); desulfonation buffer; and DNA recovery components.

The genomic sequence(s) according to SEQ ID NO: 1-10 or preferred regions thereof according to SEQ ID NO: 11-20, and non-naturally occurring treated variants thereof according to SEQ ID NO: 21-40 and 61-80 or preferred regions thereof according to SEQ ID NO: 41-60 and 81-100, were determined to have novel utility for the determination of the prognosis of a subject having cell proliferative disorder, preferably cancer.

In one embodiment the method of the invention comprises the following steps: i) determining the methylation and/or expression of at least one gene selected from the group consisting of CDO1; APC; BMPR1A; CTAGE5; CXCL12; NCR1; NFATC2; PAX9; POU4F3; and ZBTB16 and ii) determining the prognosis of a subject having cell proliferative disorder, preferably cancer. In a preferred embodiment said prognosis is the subject's prognosis subsequent to a therapy comprising at least one anthracycline.

The method of the invention may be enabled by means of any analysis of the expression of an RNA transcribed therefrom or polypeptide or protein translated from said RNA, preferably by means of mRNA expression analysis or polypeptide expression analysis. However, in the most preferred embodiment of the invention the determination of the prognosis of a subject having cell proliferative disorder, preferably cancer, is enabled by means of analysis of the methylation status of at least one gene selected from the group consisting of CDO1; APC; BMPR1A; CTAGE5; CXCL12; NCR1; NFATC2; PAX9; POU4F3; and ZBTB16, and/or promoter or regulatory elements thereof.

Accordingly the present invention also provides prognostic and/or predictive assays and methods, both quantitative and qualitative for detecting the expression of at least one gene selected from the group consisting of CDO1; APC; BMPR1A; CTAGE5; CXCL12; NCR1; NFATC2; PAX9; POU4F3; and ZBTB16 in a subject and determining therefrom the prognosis of a subject having cell proliferative disorder, preferably cancer in said subject.

Aberrant expression of mRNA transcribed from at least one gene selected from the group consisting of CDO1; APC; BMPR1A; CTAGE5; CXCL12; NCR1; NFATC2; PAX9; POU4F3; and ZBTB16 is associated with the progression of cell proliferative disorder, preferably cancer in a subject.

To detect the presence of mRNA encoding a gene or genomic sequence, a sample is obtained from the subject. The sample may be any suitable sample comprising cellular matter of the tumor. Suitable sample types include cell lines, histological slides, paraffin embedded tissues, biopsies, tissue embedded in paraffin, bodily fluids (such as but not limited to nipple aspirate and blood) and all possible combinations thereof and all possible combinations thereof. It is preferred that said sample types are cell lines, histological slides, paraffin embedded tissues, biopsies, tissue embedded in paraffin, bodily fluids (such as but not limited to nipple aspirate and blood) and all possible combinations thereof.

The sample may be treated to extract the RNA contained therein. The resulting nucleic acid from the sample is then analyzed. Many techniques are known in the state of the art for determining absolute and relative levels of gene expression, commonly used techniques suitable for use in the present invention include in situ hybridisation (e.g. FISH), Northern analysis, RNase protection assays (RPA), microarrays and PCR-based techniques, such as quantitative PCR and differential display PCR or any other nucleic acid detection method.

Particularly preferred is the use of the reverse transcription/polymerization chain reaction technique (RT-PCR). The method of RT-PCR is well known in the art (for example, see Watson and Fleming, supra).

The RT-PCR method can be performed as follows. Total cellular RNA is isolated by, for example, the standard guanidium isothiocyanate method and the total RNA is reverse transcribed. The reverse transcription method involves synthesis of DNA on a template of RNA using a reverse transcriptase enzyme and a 3' end oligonucleotide dT primer and/or random hexamer primers. The cDNA thus produced is then amplified by means of PCR. (Belyaysky et al, Nucl Acid Res 17:2919-2932, 1989; Krug and Berger, Methods in Enzymology, Academic Press, N.Y., Vol. 152, pp. 316-325, 1987 which are incorporated by reference). Further preferred is the "Real-time" variant of RT-PCR, wherein the PCR product is detected by means of hybridization probes (e.g. TaqMan, LightCycler, Molecular Beacons and Scorpion) or SYBR green. The detected signal from the probes or SYBR green is then quantitated either by reference to a standard curve or by comparing the Ct values to that of a calibration standard. Analysis of housekeeping genes is often used to normalize the results.

In Northern blot analysis total or poly(A)+ mRNA is run on a denaturing agarose gel and detected by hybridisation to a labelled probe in the dried gel itself or on a membrane. The resulting signal is proportional to the amount of target RNA in the RNA population.

Comparing the signals from two or more cell populations or tissues reveals relative differences in gene expression levels. Absolute quantitation can be performed by comparing the signal to a standard curve generated using known amounts of an in vitro transcript corresponding to the target RNA. Analysis of housekeeping genes, genes whose expression levels are expected to remain relatively constant regardless of conditions, is often used to normalize the results, eliminating any apparent differences caused by unequal transfer of RNA to the membrane or unequal loading of RNA on the gel.

The first step in Northern analysis is isolating pure, intact RNA from the cells or tissue of interest. Because Northern blots distinguish RNAs by size, sample integrity influences the degree to which a signal is localized in a single band. Partially degraded RNA samples will result in the signal being smeared or distributed over several bands with an overall loss in sensitivity and possibly an erroneous interpretation of the data. In Northern blot analysis, DNA, RNA and oligonucleotide probes can be used and these probes are preferably labelled (e.g. radioactive labels, mass labels or fluorescent labels). The size of the target RNA, not the probe, will determine the size of the detected band, so methods such as random-primed labelling, which generates probes of variable lengths, are suitable for probe synthesis. The specific activity of the probe will determine the level of sensitivity, so it is preferred that probes with high specific activities, are used.

In an RNase protection assay, the RNA target and an RNA probe of a defined length are hybridised in solution. Following hybridisation, the RNA is digested with RNases specific for single-stranded nucleic acids to remove any unhybridized, single-stranded target RNA and probe. The RNases are inactivated, and the RNA is separated e.g. by denaturing polyacrylamide gel electrophoresis. The amount of intact RNA probe is proportional to the amount of target RNA in the RNA population. RPA can be used for relative and absolute quantitation of gene expression and also for mapping RNA structure, such as intron/exon boundaries and transcription start sites. The RNase protection assay is preferable to Northern blot analysis as it generally has a lower limit of detection.

The antisense RNA probes used in RPA are generated by in vitro transcription of a DNA template with a defined endpoint and are typically in the range of 50-600 nucleotides. The use of RNA probes that include additional sequences not homologous to the target RNA allows the protected fragment to be distinguished from the full-length probe. RNA probes are typically used instead of DNA probes due to the ease of generating single-stranded RNA probes and the reproducibility and reliability of RNA:RNA duplex digestion with RNases (Ausubel et al. 2003), particularly preferred are probes with high specific activities.

Particularly preferred is the use of microarrays. The microarray analysis process can be divided into two main parts. First is the immobilization of known gene sequences onto glass slides or other solid support followed by hybridisation of the fluorescently labelled cDNA (comprising the sequences to be interrogated) to the known genes immobilized on the glass slide (or other solid phase). After hybridisation, arrays are scanned using a fluorescent microarray scanner. Analysing the relative fluorescent intensity of different genes provides a measure of the differences in gene expression.

DNA arrays can be generated by immobilizing pre-synthesized oligonucleotides onto prepared glass slides or other solid surfaces. In this case, representative gene sequences are manufactured and prepared using standard oligonucleotide synthesis and purification methods. These synthesized gene sequences are complementary to the RNA transcript(s) of at least one gene selected from the group consisting of CDO1; APC; BMPR1A; CTAGE5; CXCL12; NCR1; NFATC2; PAX9; POU4F3; and ZBTB16 and tend to be shorter sequences in the range of 25-70 nucleotides. Alternatively, immobilized oligonucleotides can be chemically synthesized in situ on the surface of the slide. In situ oligonucleotide synthesis involves the consecutive addition of the appropriate nucleotides to the spots on the microarray;

spots not receiving a nucleotide are protected during each stage of the process using physical or virtual masks. Preferably said synthesized nucleic acids are locked nucleic acids.

In expression profiling microarray experiments, the RNA templates used are representative of the transcription profile of the cells or tissues under study. RNA is first isolated from the cell populations or tissues to be compared. Each RNA sample is then used as a template to generate fluorescently labelled cDNA via a reverse transcription reaction. Fluorescent labelling of the cDNA can be accomplished by either direct labelling or indirect labelling methods. During direct labelling, fluorescently modified nucleotides (e.g., Cy®3- or Cy®5-dCTP) are incorporated directly into the cDNA during the reverse transcription. Alternatively, indirect labelling can be achieved by incorporating aminoallyl-modified nucleotides during cDNA synthesis and then conjugating an N-hydroxysuccinimide (NHS)-ester dye to the aminoallyl-modified cDNA after the reverse transcription reaction is complete. Alternatively, the probe may be unlabelled, but may be detectable by specific binding with a ligand which is labelled, either directly or indirectly. Suitable labels and methods for labelling ligands (and probes) are known in the art, and include, for example, radioactive labels which may be incorporated by known methods (e.g., nick translation or kinasing). Other suitable labels include but are not limited to biotin, fluorescent groups, chemiluminescent groups (e.g., dioxetanes, particularly triggered dioxetanes), enzymes, antibodies, and the like.

To perform differential gene expression analysis, cDNA generated from different RNA samples are labelled with Cy®3. The resulting labelled cDNA is purified to remove unincorporated nucleotides, free dye and residual RNA. Following purification, the labelled cDNA samples are hybridised to the microarray. The stringency of hybridisation is determined by a number of factors during hybridisation and during the washing procedure, including temperature, ionic strength, length of time and concentration of formamide. These factors are outlined in, for example, Sambrook et al. (Molecular Cloning: A Laboratory Manual, 2nd ed., 1989). The microarray is scanned post-hybridisation using a fluorescent microarray scanner. The fluorescent intensity of each spot indicates the level of expression of the analysed gene; bright spots correspond to strongly expressed genes, while dim spots indicate weak expression.

Once the images are obtained, the raw data must be analysed. First, the background fluorescence must be subtracted from the fluorescence of each spot. The data is then normalized to a control sequence, such as exogenously added nucleic acids (preferably RNA or DNA), or a housekeeping gene panel to account for any non-specific hybridisation, array imperfections or variability in the array set-up, cDNA labelling, hybridisation or washing. Data normalization allows the results of multiple arrays to be compared.

Another aspect of the invention relates to a kit for use in determining the prognosis of a subject having cell proliferative disorder, preferably cancer according to the methods of the present invention, said kit comprising: a means for measuring the level of transcription of at least one gene selected from the group consisting of CDO1; APC; BMPR1A; CTAGE5; CXCL12; NCR1; NFATC2; PAX9; POU4F3; and ZBTB16. In a preferred embodiment the means for measuring the level of transcription comprise oligonucleotides or polynucleotides able to hybridise under stringent or moderately stringent conditions to the transcription products of at least one gene selected from the group consisting of CDO1; APC; BMPR1A; CTAGE5; CXCL12; NCR1; NFATC2; PAX9; POU4F3; and ZBTB16. In a most preferred embodiment the level of transcription is determined by techniques selected from the group of Northern Blot analysis, reverse transcriptase PCR, real-time PCR, RNAse protection, and microarray. In another embodiment of the invention the kit further comprises means for obtaining and/or storing a biological sample of the subject. Preferred is a kit, which further comprises a container which is most preferably suitable for containing the means for measuring the level of transcription and the biological sample of the subject, and most preferably further comprises instructions for use and interpretation of the kit results.

In a preferred embodiment the kit comprises (a) a plurality of oligonucleotides or polynucleotides able to hybridise under stringent or moderately stringent conditions to the transcription products of at least one gene selected from the group consisting of CDO1; APC; BMPR1A; CTAGE5; CXCL12; NCR1; NFATC2; PAX9; POU4F3; and ZBTB16 (b) a container, preferably suitable for containing the oligonucleotides or polynucleotides and a biological sample of the subject comprising the transcription products wherein the oligonucleotides or polynucleotides can hybridise under stringent or moderately stringent conditions to the transcription products, (c) means to detect the hybridisation of (b); and optionally, (d) instructions for use and interpretation of the kit results The kit may also contain other components such as hybridisation buffer (where the oligonucleotides are to be used as a probe) packaged in a separate container. Alternatively, where the oligonucleotides are to be used to amplify a target region, the kit may contain, packaged in separate containers, a polymerase and a reaction buffer optimised for primer extension mediated by the polymerase, such as PCR. Preferably said polymerase is a reverse transcriptase. It is further preferred that said kit further contains an Rnase reagent.

The present invention further provides for methods for the detection of the presence of the polypeptide encoded by said gene sequences in a sample obtained from said subject.

Aberrant levels of polypeptide expression of the polypeptides encoded at least one gene selected from the group consisting of CDO1; APC; BMPR1A; CTAGE5; CXCL12; NCR1; NFATC2; PAX9; POU4F3; ZBTB16 are associated with the prognosis of a subject having cell proliferative disorder, preferably cancer.

According to the present invention under-expression of said polypeptides is associated with a negative prognosis of a subject having cell proliferative disorder, preferably cancer.

Any method known in the art for detecting polypeptides can be used. Such methods include, but are not limited to mass-spectrometry, immunodiffusion, immunoelectrophoresis, immunochemical methods, binder-ligand assays, immunohistochemical techniques, agglutination and complement assays (e.g., see Basic and Clinical Immunology, Sites and Terr, eds., Appleton and Lange, Norwalk, Conn. pp 217-262, 1991 which is incorporated by reference). Preferred are binder-ligand immunoassay methods including reacting antibodies with an epitope or epitopes and competitively displacing a labelled polypeptide or derivative thereof.

Certain embodiments of the present invention comprise the use of antibodies specific to the polypeptide(s) encoded by at least one gene selected from the group consisting of CDO1; APC; BMPR1A; CTAGE5; CXCL12; NCR1; NFATC2; PAX9; POU4F3; and ZBTB16.

Such antibodies are useful for determining the prognosis of a subject having cell proliferative disorder, preferably cancer. In certain embodiments production of monoclonal or polyclonal antibodies can be induced by the use of an epitope encoded by a polypeptide of at least one gene selected from the group consisting of CDO1; APC; BMPR1A; CTAGE5; CXCL12; NCR1; NFATC2; PAX9; POU4F3; and ZBTB16 as an antigen. Such antibodies may in turn be used to detect expressed polypeptides. The levels of such polypeptides present may be quantified by conventional methods. Antibody-polypeptide binding may be detected and quantified by a variety of means known in the art, such as labelling with fluorescent or radioactive ligands. The invention further comprises kits for performing the above-mentioned procedures, wherein such kits contain antibodies specific for the investigated polypeptides.

Numerous competitive and non-competitive polypeptide binding immunoassays are well known in the art. Antibodies employed in such assays may be unlabelled, for example as used in agglutination tests, or labelled for use a wide variety of assay methods. Labels that can be used include radionuclides, enzymes, fluorescers, chemiluminescers, enzyme substrates or co-factors, enzyme inhibitors, particles, dyes and the like. Preferred assays include but are not limited to radioimmunoassay (RIA), enzyme immunoassays, e.g., enzyme-linked immunosorbent assay (ELISA), fluorescent immunoassays and the like. Polyclonal or monoclonal antibodies or epitopes thereof can be made for use in immunoassays by any of a number of methods known in the art.

In an alternative embodiment of the method the proteins may be detected by means of western blot analysis. Said analysis is standard in the art, briefly proteins are separated by means of electrophoresis e.g. SDS-PAGE. The separated proteins are then transferred to a suitable membrane (or paper) e.g. nitrocellulose, retaining the spacial separation achieved by electrophoresis. The membrane is then incubated with a blocking agent to bind remaining sticky places on the membrane, commonly used agents include generic protein (e.g. milk protein). An antibody specific to the protein of interest is then added, said antibody being detectably labelled for example by dyes or enzymatic means (e.g. alkaline phosphatase or horseradish peroxidase). The location of the antibody on the membrane is then detected.

In an alternative embodiment of the method the proteins may be detected by means of immunohistochemistry (the use of antibodies to probe specific antigens in a sample). Said analysis is standard in the art, wherein detection of antigens in tissues is known as immunohistochemistry, while detection in cultured cells is generally termed immunocytochemistry. Briefly the primary antibody to be detected by binding to its specific antigen. The antibody-antigen complex is then bound by a secondary enzyme conjugated antibody. In the presence of the necessary substrate and chromogen the bound enzyme is detected according to coloured deposits at the antibody-antigen binding sites. There is a wide range of suitable sample types, antigen-antibody affinity, antibody types, and detection enhancement methods. Thus optimal conditions for immunohistochemical or immunocytochemical detection must be determined by the person skilled in the art for each individual case.

One approach for preparing antibodies to a polypeptide is the selection and preparation of an amino acid sequence of all or part of the polypeptide, chemically synthesising the amino acid sequence and injecting it into an appropriate animal, usually a rabbit or a mouse (Milstein and Kohler Nature 256:495-497, 1975; Gulfre and Milstein, Methods in Enzymology: Immunochemical Techniques 73:1-46, Langone and Banatis eds., Academic Press, 1981 which are incorporated by reference in its entirety). Methods for preparation of the polypeptides or epitopes thereof include, but are not limited to chemical synthesis, recombinant DNA techniques or isolation from biological samples.

In the final step of the method the prognosis of the subject is determined, whereby under-expression (of mRNA or polypeptides) is indicative of the prognosis of a subject having cell proliferative disorder, preferably cancer. The term under-expression shall be taken to mean expression at a detected level less than a pre-determined cut off which may be selected from the group consisting of the mean, median or an optimised threshold value. The term over-expression shall be taken to mean expression at a detected level greater than a pre-determined cut off which may be selected from the group consisting of the mean, median or an optimised threshold value.

Another aspect of the invention provides a kit for use in determining the prognosis of a subject having cell proliferative disorder, preferably cancer according to the methods of the present invention, comprising: a means for detecting at least one gene selected from the group consisting of CDO1; APC; BMPR1A; CTAGE5; CXCL12; NCR1; NFATC2; PAX9; POU4F3; and ZBTB16 polypeptides. The means for detecting the polypeptides comprise preferably antibodies, antibody derivatives, or antibody fragments. The polypeptides are most preferably detected by means of Western Blotting utilizing a labelled antibody. In another embodiment of the invention the kit further comprising means for obtaining a biological sample of the subject. Preferred is a kit, which further comprises a container suitable for containing the means for detecting the polypeptides in the biological sample of the subject, and most preferably further comprises instructions for use and interpretation of the kit results. In a preferred embodiment the kit comprises: (a) a means for detecting at least one gene selected from the group consisting of CDO1; APC; BMPR1A; CTAGE5; CXCL12; NCR1; NFATC2; PAX9; POU4F3; and ZBTB16 polypeptides; (b) a container suitable for containing the said means and the biological sample of the subject comprising the polypeptides wherein the means can form complexes with the polypeptides; (c) a means to detect the complexes of (b); and optionally (d) instructions for use and interpretation of the kit results.

The kit may also contain other components such as buffers or solutions suitable for blocking, washing or coating, packaged in a separate container.

Methylation Analysis

Particular embodiments of the present invention provide a novel application of the analysis of methylation levels and/or patterns within at least one gene selected from the group consisting of CDO1; APC; BMPR1A; CTAGE5; CXCL12; NCR1; NFATC2; PAX9; POU4F3; and ZBTB16 that enables determination of the prognosis of a subject having cell proliferative disorder, preferably cancer. Determination of the prognosis of a patient having cell proliferative disorder, preferably cancer enables the physician to make better and more informed treatment decisions. In one embodiment said prognosis is the subject's prognosis subsequent to a therapy comprising at least one anthracycline.

In the most preferred embodiment of the method, the prognosis of a subject having cell proliferative disorder, preferably cancer is determined by analysis of the methylation status of one or more CpG dinucleotides of at least one gene selected from the group consisting of CDO1; APC; BMPR1A; CTAGE5; CXCL12; NCR1; NFATC2; PAX9; POU4F3; and ZBTB16.

In one embodiment the invention of said method comprises the following steps: i) contacting genomic DNA (preferably isolated from cell lines, histological slides, paraffin embedded tissues, biopsies, tissue embedded in paraffin, bodily fluids (such as but not limited to nipple aspirate and blood) and all possible combinations thereof) obtained from the subject with at least one reagent, or series of reagents that distinguishes between methylated and non-methylated CpG dinucleotides within at least one gene selected from the group consisting of CDO1; APC; BMPR1A; CTAGE5; CXCL12; NCR1; NFATC2; PAX9; POU4F3; and ZBTB16 (including promoter and regulatory regions thereof) and ii) determining the prognosis of said subject having cell proliferative disorder, preferably cancer.

It is preferred that said one or more CpG dinucleotides of at least one gene selected from the group consisting of CDO1; APC; BMPR1A; CTAGE5; CXCL12; NCR1; NFATC2; PAX9; POU4F3; and ZBTB16 are comprised within a respective genomic target sequence thereof as provided in SEQ ID NO: 1-10, or preferred regions thereof according to SEQ ID NO: 11-20 and complements thereof. The present invention further provides a method for ascertaining genetic and/or epigenetic parameters of at least one gene selected from the group consisting of CDO1; APC; BMPR1A; CTAGE5; CXCL12; NCR1; NFATC2; PAX9; POU4F3; and ZBTB16 and/or the genomic sequence according to SEQ ID NO: 1-10, or preferred regions thereof according to SEQ ID NO: 11-20 within a subject by analyzing cytosine methylation. Said method comprising contacting a nucleic acid comprising SEQ ID NO: 1-10, or preferred regions thereof according to SEQ ID NO: 11-20 in a biological sample obtained from said subject with at least one reagent or a series of reagents, wherein said reagent or series of reagents, distinguishes between methylated and non-methylated CpG dinucleotides within the target nucleic acid.

In a preferred embodiment, said method comprises the following steps: In the first step, a sample of the tissue to be analyzed is obtained. The source may be any suitable source, such as cell lines, histological slides, paraffin embedded tissues, biopsies, tissue embedded in paraffin, bodily fluids (such as but not limited to nipple aspirate and blood) and all possible combinations thereof and all possible combinations thereof. It is preferred that said sources of DNA are cell lines, histological slides, paraffin embedded tissues, biopsies, tissue embedded in paraffin, bodily fluids (such as but not limited to nipple aspirate and blood) and all possible combinations thereof.

The genomic DNA is then isolated from the sample. Genomic DNA may be isolated by any means standard in the art, including the use of commercially available kits. Briefly, wherein the DNA of interest is encapsulated in by a cellular membrane the biological sample must be disrupted and lysed by enzymatic, chemical or mechanical means. The DNA solution may then be cleared of proteins and other contaminants e.g. by digestion with proteinase K. The genomic DNA is then recovered from the solution. This may be carried out by means of a variety of methods including salting out, organic extraction or binding of the DNA to a solid phase support. The choice of method will be affected by several factors including time, expense and required quantity of DNA.

Wherein the sample DNA is not enclosed in a membrane (e.g. circulating DNA from a blood sample) methods standard in the art for the isolation and/or purification of DNA may be employed. Such methods include the use of a protein degenerating reagent e.g. chaotropic salt e.g. guanidine hydrochloride or urea; or a detergent e.g. sodium dodecyl sulphate (SDS), cyanogen bromide. Alternative methods include but are not limited to ethanol precipitation or propanol precipitation, vacuum concentration amongst others by means of a centrifuge. The person skilled in the art may also make use of devices such as filter devices e.g. ultrafiltration, silica surfaces or membranes, magnetic particles, polystyrene particles, polystyrene surfaces, positively charged surfaces, and positively charged membranes, charged membranes, charged surfaces, charged switch membranes, charged switched surfaces.

Once the nucleic acids have been extracted, the genomic double stranded DNA is used in the analysis, methylation analysis may be carried out by any means known in the art including but not limited to methylation sensitive restriction enzyme analysis and chemical reagent analysis.

Chemical Analysis

In the second step of the method, the genomic DNA sample is treated in such a manner that cytosine bases which are unmethylated at the 5'-position are converted to uracil, thymine, or another base which is dissimilar to cytosine in terms of hybridization behavior. This will be understood as 'pre-treatment' or 'treatment' herein.

This is preferably achieved by means of treatment with a bisulfite reagent. The term "bisulfite reagent" refers to a reagent comprising bisulfite, disulfite, hydrogen sulfite or combinations thereof, useful as disclosed herein to distinguish between methylated and unmethylated CpG dinucleotide sequences. Methods of said treatment are known in the art (e.g. PCT/EP2004/011715, which is incorporated by reference in its entirety). It is preferred that the bisulfite treatment is conducted in the presence of denaturing solvents such as but not limited to n-alkylenglycol, particularly diethylene glycol dimethyl ether (DME), or in the presence of dioxane or dioxane derivatives. In a preferred embodiment the denaturing solvents are used in concentrations between 1% and 35% (v/v). It is also preferred that the bisulfite reaction is carried out in the presence of scavengers such as but not limited to chromane derivatives, e.g., 6-hydroxy-2, 5,7,8, -tetramethylchromane 2-carboxylic acid or trihydroxybenzoe acid and derivates thereof, e.g. Gallic acid (see: PCT/EP2004/011715 which is incorporated by reference in its entirety). The bisulfite conversion is preferably carried out at a reaction temperature between 30° C. and 70° C., whereby the temperature is increased to over 85° C. for short periods of times during the reaction (see: PCT/EP2004/011715 which is incorporated by reference in its entirety). The bisulfite treated DNA is preferably purified priori to the quantification. This may be conducted by any means known in the art, such as but not limited to ultrafiltration, preferably carried out by means of Microcon^™ columns (manufactured by Millipore^™). The purification is carried out according to a modified manufacturer's protocol (see: WO 2005/038051 which is incorporated by reference in its entirety).

In the third step of the method, fragments of the treated DNA are amplified, using sets of primer oligonucleotides according to the present invention, and an amplification enzyme. The amplification of several DNA segments can be carried out simultaneously in one and the same reaction vessel. Typically, the amplification is carried out using a polymerase chain reaction (PCR). Preferably said amplificates are 100 to 2,000 base pairs in length. The set of primer oligonucleotides includes at least two oligonucleotides whose sequences are each reverse complementary, identical, or hybridize under stringent or highly stringent conditions to an at least 16-base-pair long segment of the base sequences of one of SEQ ID NO: 21-40 and 61-80 or preferred regions thereof according to SEQ ID NO: 41-60 and 81-100 and sequences complementary thereto.

In an alternate embodiment of the method, the methylation status of pre-selected CpG positions within at least one gene selected from the group consisting of CDO1; APC; BMPR1A; CTAGE5; CXCL12; NCR1; NFATC2; PAX9; POU4F3; and ZBTB16 and preferably within the nucleic acid sequences according to SEQ ID NO: 1-10, or preferred regions thereof according to SEQ ID NO: 11-20, may be detected by use of methylation-specific primer oligonucleotides. This technique (MSP) has been described in U.S. Pat. No. 6,265,171 to Herman. The use of methylation status specific primers for the amplification of bisulfite treated DNA allows the differentiation between methylated and unmethylated nucleic acids. MSP primers pairs contain at least one primer which hybridizes to a bisulfite treated CpG dinucleotide. Therefore, the sequence of said primers comprises at least one CpG dinucleotide. MSP primers specific for non-methylated DNA contain a "T" at the position of the C position in the CpG. Preferably, therefore, the base sequence of said primers is required to comprise a sequence having a length of at least 9 nucleotides which hybridizes to a treated nucleic acid sequence according to one of SEQ ID NO: 21-40 and 61-80 or preferred regions thereof according to SEQ ID NO: 41-60 and 81-100 and sequences complementary thereto, wherein the base sequence of said oligomers comprises at least one CpG dinucleotide.A further preferred embodiment of the method comprises the use of blocker oligonucleotides (the HeavyMethyl™ assay). The use of such blocker oligonucleotides has been described by Yu et al., BioTechniques 23:714-720, 1997. Blocking probe oligonucleotides are hybridized to the bisulfite treated nucleic acid concurrently with the PCR primers. PCR amplification of the nucleic acid is terminated at the 5' position of the blocking probe, such that amplification of a nucleic acid is suppressed where the complementary sequence to the blocking probe is present. The probes may be designed to hybridize to the bisulfite treated nucleic acid in a methylation status specific manner. For example, for detection of methylated nucleic acids within a population of unmethylated nucleic acids, suppression of the amplification of nucleic acids which are unmethylated at the position in question would be carried out by the use of blocking probes comprising a 'CpA' or 'TpA' at the position in question, as opposed to a 'CpG' if the suppression of amplification of methylated nucleic acids is desired.

For PCR methods using blocker oligonucleotides, efficient disruption of polymerase-mediated amplification requires that blocker oligonucleotides not be elongated by the polymerase. Preferably, this is achieved through the use of blockers that are 3'-deoxyoligonucleotides, or oligonucleotides derivitized at the 3' position with other than a "free" hydroxyl group. For example, 3'-O-acetyl oligonucleotides are representative of a preferred class of blocker molecule.

Additionally, polymerase-mediated decomposition of the blocker oligonucleotides should be precluded. Preferably, such preclusion comprises either use of a polymerase lacking 5'-3' exonuclease activity, or use of modified blocker oligonucleotides having, for example, thioate bridges at the 5'-terminii thereof that render the blocker molecule nuclease-resistant. Particular applications may not require such 5' modifications of the blocker. For example, if the blocker- and primer-binding sites overlap, thereby precluding binding of the primer (e.g., with excess blocker), degradation of the blocker oligonucleotide will be substantially precluded. This is because the polymerase will not extend the primer toward, and through (in the 5'-3' direction) the blocker—a process that normally results in degradation of the hybridized blocker oligonucleotide.

A particularly preferred blocker/PCR embodiment, for purposes of the present invention and as implemented herein, comprises the use of peptide nucleic acid (PNA) oligomers as blocking oligonucleotides. Such PNA blocker oligomers are ideally suited, because they are neither decomposed nor extended by the polymerase.

Preferably, therefore, the base sequence of said blocking oligonucleotides is required to comprise a sequence having a length of at least 9 nucleotides which hybridizes to a treated nucleic acid sequence according to one of SEQ ID NO: 21-40 and 61-80 or preferred regions thereof according to SEQ ID NO: 41-60 and 81-100 and sequences complementary thereto, wherein the base sequence of said oligonucleotides comprises at least one CpG, TpG or CpA dinucleotide. It is particularly preferred that the base sequence of said blocking oligonucleotides is required to comprise a sequence having a length of at least 9 nucleotides which hybridizes to a treated nucleic acid sequence according to one of SEQ ID NO: 61-80 or preferred regions thereof according to SEQ ID NO: 81-100 and sequences complementary thereto, wherein the base sequence of said oligonucleotides comprises at least one TpG or CpA dinucleotide.

The fragments obtained by means of the amplification can carry a directly or indirectly detectable label. Preferred are labels in the form of fluorescence labels, radionuclides, or detachable molecule fragments having a typical mass which can be detected in a mass spectrometer. Where said labels are mass labels, it is preferred that the labeled amplificates have a single positive or negative net charge, allowing for better delectability in the mass spectrometer. The detection may be carried out and visualized by means of, e.g., matrix assisted laser desorption/ionization mass spectrometry (MALDI) or using electron spray mass spectrometry (ESI).

Matrix Assisted Laser Desorption/Ionization Mass Spectrometry (MALDI-TOF) is a very efficient development for the analysis of biomolecules (Karas and Hillenkamp, Anal Chem., 60:2299-301, 1988). An analyte is embedded in a light-absorbing matrix. The matrix is evaporated by a short laser pulse thus transporting the analyte molecule into the vapor phase in an unfragmented manner. The analyte is ionized by collisions with matrix molecules. An applied voltage accelerates the ions into a field-free flight tube. Due to their different masses, the ions are accelerated at different rates. Smaller ions reach the detector sooner than bigger ones. MALDI-TOF spectrometry is well suited to the analysis of peptides and proteins. The analysis of nucleic acids is somewhat more difficult (Gut and Beck, Current Innovations and Future Trends, 1:147-57, 1995). The sensitivity with respect to nucleic acid analysis is approximately 100-times less than for peptides, and decreases disproportionally with increasing fragment size. Moreover, for nucleic acids having a multiply negatively charged backbone, the ionization process via the matrix is considerably less efficient. In MALDI-TOF spectrometry, the selection of the matrix plays an eminently important role. For desorption of peptides, several very efficient matrixes have been found which produce a very fine crystallization. There are now several responsive matrixes for DNA, however, the difference in sensitivity between peptides and nucleic acids has not been reduced. This difference in sensitivity can be reduced, however, by chemically modifying the DNA in such a manner that it becomes more similar to a peptide. For example, phosphorothioate nucleic acids, in which the usual phosphates of the backbone are substituted with thiophosphates, can be converted into a charge-neutral DNA using simple alkylation chemistry (Gut and Beck, *Nucleic Acids Res.* 23: 1367-73, 1995). The coupling of a charge tag to this modified DNA results in an increase in MALDI-TOF sensitivity to the same level as that found for peptides. A further advantage of charge tagging is the increased stability of the analysis against impurities, which makes the detection of unmodified substrates considerably more difficult.

In the fourth step of the method, the amplificates obtained during the third step of the method are analyzed in order to ascertain the methylation status of the CpG dinucleotides prior to the treatment.

In embodiments where the amplificates were obtained by means of MSP amplification, the presence, absence or class of an amplificate is in itself indicative of the methylation state of the CpG positions covered by the primer, according to the base sequences of said primer.

Amplificates obtained by means of both standard and methylation specific PCR may be further analyzed by means of based-based methods such as, but not limited to, array technology and probe based technologies as well as by means of techniques such as sequencing and template directed extension.

In one embodiment of the method, the amplificates synthesized in step three are subsequently hybridized to an array or a set of oligonucleotides and/or PNA probes. In this context, the hybridization takes place in the following manner: the set of probes used during the hybridization is preferably composed of at least 2 oligonucleotides or PNA-oligomers; in the process, the amplificates serve as probes which hybridize to oligonucleotides previously bonded to a solid phase; the non-hybridized fragments are subsequently removed; said oligonucleotides contain at least one base sequence having a length of at least 9 nucleotides which is reverse complementary or identical to a segment of the base sequences specified in the present Sequence Listing; and the segment comprises at least one CpG, TpG or CpA dinucleotide. The hybridizing portion of the hybridizing nucleic acids is typically at least 9, 15, 20, 25, 30 or 35 nucleotides in length. However, longer molecules have inventive utility, and are thus within the scope of the present invention.

In a preferred embodiment, said dinucleotide is present in the central third of the oligomer. For example, wherein the oligomer comprises one CpG dinucleotide, said dinucleotide is preferably the fifth to ninth nucleotide from the 5'-end of a 13-mer. One oligonucleotide exists for the analysis of each CpG dinucleotide within a sequence selected from the group consisting SEQ ID NO: 1-10, or preferred regions thereof according to SEQ ID NO: 11-20, and the equivalent positions within SEQ ID NO: 21-40 and 61-80 or preferred regions thereof according to SEQ ID NO: 41-60 and 81-100. Said oligonucleotides may also be present in the form of peptide nucleic acids. The non-hybridized amplificates are then removed. The hybridized amplificates are then detected. In this context, it is preferred that labels attached to the amplificates are identifiable at each position of the solid phase at which an oligonucleotide sequence is located.

In yet a further embodiment of the method, the genomic methylation status of the CpG positions may be ascertained by means of oligonucleotide probes (as detailed above) that are hybridized to the bisulfite treated DNA concurrently with the PCR amplification primers (wherein said primers may either be methylation specific or standard).

A particularly preferred embodiment of this method is the use of fluorescence-based Real Time Quantitative PCR (Heid et al., *Genome Res.* 6:986-994, 1996; also see U.S. Pat. No. 6,331,393) employing a dual-labeled fluorescent oligonucleotide probe (TaqMan™ PCR, using an ABI Prism 7700 Sequence Detection System, Perkin Elmer Applied Biosystems, Foster City, Calif.). The TaqMan™ PCR reaction employs the use of a non-extendible interrogating oligonucleotide, called a TaqMan™ probe, which, in preferred embodiments, is designed to hybridize to a CpG-rich sequence located between the forward and reverse amplification primers. The TaqMan™ probe further comprises a fluorescent "reporter moiety" and a "quencher moiety" covalently bound to linker moieties (e.g., phosphoramidites) attached to the nucleotides of the TaqMan™ oligonucleotide. For analysis of methylation within nucleic acids subsequent to bisulfite treatment, it is required that the probe be methylation specific, as described in U.S. Pat. No. 6,331,393, (hereby incorporated by reference in its entirety) also known as the MethyLightTM™ assay. Variations on the TaqMann™ detection methodology that are also suitable for use with the described invention include the use of dual-probe technology (LightCycler™) or fluorescent amplification primers (Sunrise™ technology). Both these techniques may be adapted in a manner suitable for use with bisulfite treated DNA, and moreover for methylation analysis within CpG dinucleotides.

In a further preferred embodiment of the method, the fourth step of the method comprises the use of template-directed oligonucleotide extension, such as MS-SNuPE as described by Gonzalgo and Jones, *Nucleic Acids Res.* 25:2529-2531, 1997.

In yet a further embodiment of the method, the fourth step of the method comprises sequencing and subsequent sequence analysis of the amplificate generated in the third step of the method (Sanger F., et al., *Proc Natl Acad Sci USA* 74:5463-5467, 1977).

In the most preferred embodiment of the method the genomic nucleic acids are isolated and treated according to the first three steps of the method outlined above, namely:
  a) obtaining, from a subject, a biological sample having subject genomic DNA;
  b) extracting or otherwise isolating the genomic DNA;
  c) treating the genomic DNA of b), or a fragment thereof, with one or more reagents to convert cytosine bases that are unmethylated in the 5-position thereof to uracil or to another base that is detectably dissimilar to cytosine in terms of hybridization properties; and wherein
  d) amplifying subsequent to treatment in c) is carried out in a methylation specific manner, namely by use of methylation specific primers or blocking oligonucleotides, and further wherein
  e) detecting of the amplificates is carried out by means of a real-time detection probe, as described above.

Preferably, where the subsequent amplification of d) is carried out by means of methylation specific primers, as described above, said methylation specific primers comprise a sequence having a length of at least 9 nucleotides which hybridizes to a treated nucleic acid sequence according to one of SEQ ID NO: 21-40 and 61-80 or preferred regions thereof according to SEQ ID NO: 41-60 and 81-100 and sequences complementary thereto, wherein the base sequence of said oligomers comprise at least one CpG dinucleotide.

Step e) of the method, namely the detection of the specific amplificates indicative of the methylation status of one or more CpG positions according to SEQ ID NO: 1-10, or preferred regions thereof according to SEQ ID NO: 11-20 is carried out by means of real-time detection methods as described above.

Methylation Sensitive Restriction Enzyme Analysis

In an alternative embodiment of the invention the above described second step may be carried out by means of methylation sensitive or methylation specific restriction enzyme analysis. Methods are known in the art wherein a methylation sensitive restriction enzyme reagent, or a series of restriction enzyme reagents comprising methylation sensitive restriction enzyme reagents that distinguishes between methylated and non-methylated CpG dinucleotides within a target region are utilized in determining methylation, for example but not limited to DMH.

In a preferred embodiment, the DNA may be cleaved prior to treatment with methylation sensitive restriction enzymes. Such methods are known in the art and may include both physical and enzymatic means. Particularly preferred is the use of one or a plurality of restriction enzymes which are not methylation sensitive, and whose recognition sites are AT rich and do not comprise CG dinucleotides. The use of such enzymes enables the conservation of CpG islands and CpG rich regions in the fragmented DNA. The non-methylation-specific restriction enzymes are preferably selected from the group consisting of MseI, BfaI, Csp6I, Tru1I, Tvu1I, Tru9I, Tvu9I, MaeI and XspI. Particularly preferred is the use of two or three such enzymes. Particularly preferred is the use of a combination of MseI, BfaI and Csp6I.

The fragmented DNA may then be ligated to adaptor oligonucleotides in order to facilitate subsequent enzymatic amplification. The ligation of oligonucleotides to blunt and sticky ended DNA fragments is known in the art, and is carried out by means of dephosphorylation of the ends (e.g. using calf or shrimp alkaline phosphatase) and subsequent ligation using ligase enzymes (e.g. T4 DNA ligase) in the presence of dATPs. The adaptor oligonucleotides are typically at least 18 base pairs in length.

In the third step, the DNA (or fragments thereof) is then digested with one or more methylation sensitive restriction enzymes. The digestion is carried out such that hydrolysis of the DNA at the restriction site is informative of the methylation status of a specific CpG dinucleotide of at least one gene selected from the group consisting of CDO1; APC; BMPR1A; CTAGE5; CXCL12; NCR1; NFATC2; PAX9; POU4F3; and ZBTB16.

Preferably, the methylation-specific restriction enzyme is selected from the group consisting of Bsi EI, Hga I HinPI, Hpy99I, Ave I, Bce AI, Bsa HI, BisI, BstUI, Bsh1236I, AccII, BstFNI, McrBC, GlaI, MvnI, HpaII (HapII), HhaI, AciI, SmaI, HinP1I, HpyCH4IV, EagI and mixtures of two or more of the above enzymes. Preferred is a mixture containing the restriction enzymes BstUI, HpaII, HpyCH4IV and HinP1I.

In the fourth step, which is optional but a preferred embodiment, the restriction fragments are amplified. This is preferably carried out using a polymerase chain reaction, and said amplificates may carry suitable detectable labels as discussed above, namely fluorophore labels, radionuclides and mass labels. Particularly preferred is amplification by means of an amplification enzyme and at least two primers comprising, in each case a contiguous sequence at least 16 nucleotides in length that is complementary to, or hybridizes under moderately stringent or stringent conditions to a sequence selected from the group consisting SEQ ID NO: 1-10, or preferred regions thereof according to SEQ ID NO: 11-20, and complements thereof. Preferably said contiguous sequence is at least 16, 20 or 25 nucleotides in length. In an alternative embodiment said primers may be complementary to any adaptors linked to the fragments.

In the fifth step the amplificates are detected. The detection may be by any means standard in the art, for example, but not limited to, gel electrophoresis analysis, hybridization analysis, incorporation of detectable tags within the PCR products, DNA array analysis, MALDI or ESI analysis. Preferably said detection is carried out by hybridization to at least one nucleic acid or peptide nucleic acid comprising in each case a contiguous sequence at least 16 nucleotides in length that is complementary to, or hybridizes under moderately stringent or stringent conditions to a sequence selected from the group consisting SEQ ID NO: 1-10, or preferred regions thereof according to SEQ ID NO: 11-20, and complements thereof. Preferably said contiguous sequence is at least 16, 20 or 25 nucleotides in length.

Subsequent to the determination of the methylation state or level of the genomic nucleic acids the prognosis of a subject having cell proliferative disorder, preferably cancer, is deduced based upon the methylation state or level of at least one CpG dinucleotide sequence of CDO1; APC; BMPR1A; CTAGE5; CXCL12; NCR1; NFATC2; PAX9; POU4F3; and ZBTB16, or an average, or a value reflecting an average methylation state of a plurality of CpG dinucleotide sequences of SEQ ID NO: 1-10, or preferred regions thereof according to SEQ ID NO: 11-20 wherein methylation is associated with the prognosis of a subject having cell proliferative disorder, preferably cancer. Said methylation is in particular associated with the subject's prognosis subsequent to a therapy comprising at least one anthracycline. Wherein said methylation is determined by quantitative means the cut-off point for determining said presence of methylation is preferably zero (i.e. wherein a sample displays any degree of methylation it is determined as having a methylated status at the analyzed CpG position). Nonetheless, it is foreseen that the person skilled in the art may wish to adjust said cut-off value in order to provide an assay of a particularly preferred sensitivity or specificity. Accordingly said cut-off value may be increased (thus increasing the specificity), said cut off value may be within a range selected form the group consisting of 0%-5%, 5%-10%, 10%-15%, 15%-20%, 20%-30% and 30%-50%. Particularly preferred are cut-offs that are at least 0.1%, 1%, 10%, 15%, 25%, and 30%.

Upon determination of the methylation and/or expression of the at least one gene selected from the group consisting of CDO1; APC; BMPR1A; CTAGE5; CXCL12; NCR1; NFATC2; PAX9; POU4F3; and ZBTB16 the prognosis of the subject is determined. Methylation, hyper-methylation and/or under-expression of the genes APC; BMPR1A; CDO1; CTAGE5; CXCL12; PAX9; POU4F3; and ZBTB16 indicates a negative prognosis of said subject as compared to subjects presenting zero methylation, hypo-methylation and/or over-expression. Conversely methylation, hyper-methylation and/or under-expression of the genes NCR1; NFATC2; indicates a positive prognosis of said subject as compared to subjects presenting zero methylation, hypo-methylation and/or over-expression.

As used herein the term "prognosis" shall be taken to mean an indicator of the predicted progression of the disease (including but not limited to aggressiveness and metastatic potential) and/or predicted patient survival time.

In the context of the present invention the term 'aggressiveness' is taken to mean one or more of high likelihood of relapse post surgery; below average or below median patient survival; below average or below median disease free survival; below average or below median relapse-free survival; above average tumor-related complications; fast progression of tumor or metastases.

Unless stated otherwise as used herein the term "survival" shall be taken to include all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g. time of diagnosis or start of treatment) and end point (e.g. death, recurrence or metastasis).

Further Improvements

The disclosed invention provides treated nucleic acids, derived from genomic SEQ ID NO: 1-10, or preferred regions thereof according to SEQ ID NO: 11-20, wherein the treatment is suitable to convert at least one unmethylated cytosine base of the genomic DNA sequence to uracil or another base that is detectably dissimilar to cytosine in terms of hybridization. The genomic sequences in question may comprise one, or more consecutive methylated CpG positions. Said treatment preferably comprises use of a reagent selected from the group consisting of bisulfite, hydrogen sulfite, disulfite, and combinations thereof. In a preferred embodiment of the invention, the invention provides a non-naturally occurring modified nucleic acid comprising a sequence of at least 16 contiguous nucleotide bases in length of a sequence selected from the group consisting of SEQ ID NO: 21-40 and 61-80 or preferred regions thereof according to SEQ ID NO: 41-60 and 81-100. In further preferred embodiments of the invention said nucleic acid is at least 50, 100, 150, 200, 250 or 500 base pairs in length of a segment of the nucleic acid sequence disclosed in SEQ ID NO: 21-40 and 61-80 or preferred regions thereof according to SEQ ID NO: 41-60 and 81-100. Particularly preferred is a nucleic acid molecule that is identical or complementary to all or a portion of the sequences SEQ ID NO: 21-40 and 61-80 or preferred regions thereof according to SEQ ID NO: 41-60 and 81-100 but not SEQ ID NO: 1-10, or preferred regions thereof according to SEQ ID NO: 11-20 or other naturally occurring DNA.

It is preferred that said sequence comprises at least one CpG, TpA or CpA dinucleotide and sequences complementary thereto. The sequences of SEQ ID NO: 21-40 and 61-80 or preferred regions thereof according to SEQ ID NO: 41-60 and 81-100 provide non-naturally occurring modified versions of the nucleic acid according to SEQ ID NO: 1-10 or preferred regions thereof according to SEQ ID NO: 11-20, wherein the modification of each genomic sequence results in the synthesis of a nucleic acid having a sequence that is unique and distinct from said genomic sequence as follows. For each sense strand genomic DNA, e.g., SEQ ID NO: 1-10, or preferred regions thereof according to SEQ ID NO: 11-20, four converted versions are disclosed. A first version wherein "C" is converted to "T," but "CpG" remains "CpG" (i.e., corresponds to case where, for the genomic sequence, all "C" residues of CpG dinucleotide sequences are methylated and are thus not converted); a second version discloses the complement of the disclosed genomic DNA sequence (i.e. antisense strand), wherein "C" is converted to "T," but "CpG" remains "CpG" (i.e., corresponds to case where, for all "C" residues of CpG dinucleotide sequences are methylated and are thus not converted). The 'upmethylated' converted sequences of SEQ ID NO: 1-10, or preferred regions thereof according to SEQ ID NO: 11-20 correspond to SEQ ID NO: 21-40 or preferred regions thereof according to SEQ ID NO: 41-60. A third chemically converted version of each genomic sequences is provided, wherein "C" is converted to "T" for all "C" residues, including those of "CpG" dinucleotide sequences (i.e., corresponds to case where, for the genomic sequences, all "C" residues of CpG dinucleotide sequences are unmethylated); a final chemically converted version of each sequence, discloses the complement of the disclosed genomic DNA sequence (i.e. antisense strand), wherein "C" is converted to "T" for all "C" residues, including those of "CpG" dinucleotide sequences (i.e., corresponds to case where, for the complement (antisense strand) of each genomic sequence, all "C" residues of CpG dinucleotide sequences are unmethylated). The 'downmethylated' converted sequences of SEQ ID NO: 1-10, or preferred regions thereof according to SEQ ID NO: 11-20 corresponds to SEQ ID NO: 61-80 or preferred regions thereof according to SEQ ID NO: 81-100.

Significantly, heretofore, the nucleic acid sequences and molecules according SEQ ID NO: 21-40 and 61-80 or preferred regions thereof according to SEQ ID NO: 41-60 and 81-100 were not implicated in or connected with the prognosis of a subject having cell proliferative disorder, preferably cancer.

In an alternative preferred embodiment, the invention further provides oligonucleotides or oligomers suitable for use in the methods of the invention for detecting the cytosine methylation state within genomic or treated (chemically modified) DNA, according to SEQ ID NO: 1-100. Said oligonucleotide or oligomer nucleic acids provide novel prognostic and/or predictive means. Said oligonucleotide or oligomer comprising a nucleic acid sequence having a length of at least nine (9) nucleotides which is identical to, hybridizes, under moderately stringent or stringent conditions (as defined herein above), to a treated nucleic acid sequence according to SEQ ID NO: 21-40 and 61-80 or preferred regions thereof according to SEQ ID NO: 41-60 and 81-100 and/or sequences complementary thereto, or to a genomic sequence according to SEQ ID NO: 1-10, or preferred regions thereof according to SEQ ID NO: 11-20 and/or sequences complementary thereto.

Thus, the present invention includes nucleic acid molecules (e.g., oligonucleotides and peptide nucleic acid (PNA) molecules (PNA-oligomers)) that hybridize under moderately stringent and/or stringent hybridization conditions to all or a portion of the sequences SEQ ID NO: 1-100 or to the complements thereof. Particularly preferred is a nucleic acid molecule that hybridizes under moderately stringent and/or stringent hybridization conditions to all or a portion of the sequences SEQ ID NO: 21-40 and 61-80 or preferred regions thereof according to SEQ ID NO: 41-60 and 81-100 but not SEQ ID NO: 1-10, or preferred regions thereof according to SEQ ID NO: 11-20 or other human genomic DNA.

The identical or hybridizing portion of the hybridizing nucleic acids is typically at least 9, 16, 20, 25, 30 or 35 nucleotides in length. However, longer molecules have inventive utility, and are thus within the scope of the present invention.

Preferably, the hybridizing portion of the inventive hybridizing nucleic acids is at least 95%, or at least 98%, or 100% identical to the sequence, or to a portion thereof of SEQ ID NO: 1-100, or to the complements thereof.

Hybridizing nucleic acids of the type described herein can be used, for example, as a primer (e.g., a PCR primer), or a prognostic and/or predictive probe or primer. Preferably, hybridization of the oligonucleotide probe to a nucleic acid sample is performed under stringent conditions and the probe is 100% identical to the target sequence. Nucleic acid duplex or hybrid stability is expressed as the melting temperature or Tm, which is the temperature at which a probe dissociates from a target DNA. This melting temperature is used to define the required stringency conditions.

For target sequences that are related and substantially identical to the corresponding sequence of SEQ ID NO: 1-10, or preferred regions thereof according to SEQ ID NO: 11-20 (such as allelic variants and SNPs), rather than identical, it is useful to first establish the low-est temperature at which only homologous hybridization occurs with a particular concentration of salt (e.g., SSC or SSPE). Then, assuming that 1% mismatching results in a 1° C. decrease in the Tm, the temperature of the final wash in the hybridization reaction is reduced accordingly (for example, if sequences having >95% identity with the probe are sought, the final wash temperature is decreased by 5° C.). In practice, the change in Tm can be between 0.5° C. and 1.5° C. per 1% mismatch.

Examples of inventive oligonucleotides of length X (in nucleotides), as indicated by polynucleotide positions with reference to, e.g., SEQ ID NO: 1, include those corresponding to sets (sense and antisense sets) of consecutively overlapping oligonucleotides of length X, where the oligonucleotides within each consecutively overlapping set (corresponding to a given X value) are defined as the finite set of Z oligonucleotides from nucleotide positions: n to (n+(X−1)); where n=1, 2, 3, . . . (Y−(X−1)); where Y equals the length (nucleotides or base pairs) of SEQ ID NO: 1 (18012); where X equals the common length (in nucleotides) of each oligonucleotide in the set (e.g., X=20 for a set of consecutively overlapping 20-mers); and where the number (Z) of consecutively overlapping oligomers of length X for a given SEQ ID NO: 1 of length Y is equal to Y−(X−1). For example Z=18012−19=17993 for either sense or antisense sets of SEQ ID NO: 1, where X=20.

Preferably, the set is limited to those oligomers that comprise at least one CpG, TpG or CpA dinucleotide.

Examples of inventive 20-mer oligonucleotides include the following set of 17993 oligomers (and the antisense set complementary thereto), indicated by polynucleotide positions with reference to SEQ ID NO: 1:1-20, 2-21, 3-22, 4-23, 5-24, . . . and 17993-18012

Preferably, the set is limited to those oligomers that comprise at least one CpG, TpG or CpA dinucleotide.

Likewise, examples of inventive 25-mer oligonucleotides include the following set of 17988 oligomers (and the antisense set complementary thereto), indicated by polynucleotide positions with reference to SEQ ID NO: 1:1-25, 2-26, 3-27, 4-28, 5-29, . . . and 17988-18012.

Preferably, the set is limited to those oligomers that comprise at least one CpG, TpG or CpA dinucleotide.

The present invention encompasses, for each of SEQ ID NO: 1-100 (sense and antisense), multiple consecutively overlapping sets of oligonucleotides or modified oligonucleotides of length X, where, e.g., X=9, 10, 17, 20, 22, 23, 25, 27, 30 or 35 nucleotides.

The oligonucleotides or oligomers according to the present invention constitute effective tools useful to ascertain genetic and epigenetic parameters of the genomic sequence corresponding to SEQ ID NO: 1-10, or preferred regions thereof according to SEQ ID NO: 11-20. Preferred sets of such oligonucleotides or modified oligonucleotides of length X are those consecutively overlapping sets of oligomers corresponding to SEQ ID NO: 1-100 (and to the complements thereof). Preferably, said oligomers comprise at least one CpG, TpG or CpA dinucleotide.

Particularly preferred oligonucleotides or oligomers according to the present invention are those in which the cytosine of the CpG dinucleotide (or of the corresponding converted TpG or CpA dinucleotide) sequences is within the middle third of the oligonucleotide; that is, where the oligonucleotide is, for example, 13 bases in length, the CpG, TpG or CpA dinucleotide is positioned within the fifth to ninth nucleotide from the 5'-end.

The oligonucleotides of the invention can also be modified by chemically linking the oligonucleotide to one or more moieties or conjugates to enhance the activity, stability or detection of the oligonucleotide. Such moieties or conjugates include chromophores, fluorophors, lipids such as cholesterol, cholic acid, thioether, aliphatic chains, phospholipids, polyamines, polyethylene glycol (PEG), palmityl moieties, and others as disclosed in, for example, U.S. Pat. Nos. 5,514,758, 5,565,552, 5,567,810, 5,574,142, 5,585, 481, 5,587,371, 5,597,696 and 5,958,773. The probes may also exist in the form of a PNA (peptide nucleic acid) which has particularly preferred pairing properties. Thus, the oligonucleotide may include other appended groups such as peptides, and may include hybridization-triggered cleavage agents (Krol et al., *BioTechniques* 6:958-976, 1988) or intercalating agents (Zon, Pharm. Res. 5:539-549, 1988). To this end, the oligonucleotide may be conjugated to another molecule, e.g., a chromophore, fluorophor, peptide, hybridization-triggered cross-linking agent, transport agent, hybridization-triggered cleavage agent, etc.

The oligonucleotide may also comprise at least one art-recognized modified sugar and/or base moiety, or may comprise a modified backbone or non-natural internucleoside linkage. The oligonucleotides or oligomers according to particular embodiments of the present invention are typically used in 'sets,' which contain at least one oligomer for analysis of each of the CpG dinucleotides of a genomic sequence selected from the group consisting SEQ ID NO: 1-10, or preferred regions thereof according to SEQ ID NO: 11-20 and sequences complementary thereto, or to the corresponding CpG, TpG or CpA dinucleotide within a sequence of the treated nucleic acids according to SEQ ID NO: 21-40 and 61-80 or preferred regions thereof according to SEQ ID NO: 41-60 and 81-100 and sequences complementary thereto. However, it is anticipated that for economic or other factors it may be preferable to analyse a limited selection of the CpG dinucleotides within said sequences, and the content of the set of oligonucleotides is altered accordingly.

Therefore, in particular embodiments, the present invention provides a set of at least two (2) (oligonucleotides and/or PNA-oligomers) useful for detecting the cytosine methylation state in treated genomic DNA (SEQ ID NO: 21-40 and 61-80 or preferred regions thereof according to SEQ ID NO: 41-60 and 81-100), or in genomic DNA (SEQ ID NO: 1-10, or preferred regions thereof according to SEQ ID NO: 11-20 and sequences complementary thereto). These probes enable determination of the prognosis of a subject having cell proliferative disorder, preferably cancer. The set of oligomers may also be used for detecting single nucleotide polymorphisms (SNPs) in treated genomic DNA (SEQ ID NO: 21-40 and 61-80 or preferred regions thereof according to SEQ ID NO: 41-60 and 81-100), or in genomic DNA (SEQ ID NO: 1-10, or preferred regions thereof according to SEQ ID NO: 11-20 and sequences complementary thereto).

In preferred embodiments, at least one, and more preferably all members of a set of oligonucleotides is bound to a solid phase.

In further embodiments, the present invention provides a set of at least two (2) oligonucleotides that are used as 'primer' oligonucleotides for amplifying DNA sequences of one of SEQ ID NO: 1-100 and sequences complementary thereto, or segments thereof.

It is anticipated that the oligonucleotides may constitute all or part of an "array" or "DNA chip" (i.e., an arrangement of different oligonucleotides and/or PNA-oligomers bound to a solid phase). Such an array of different oligonucleotide- and/or PNA-oligomer sequences can be characterized, for example, in that it is arranged on the solid phase in the form of a rectangular or hexagonal lattice. The solid-phase surface may be composed of silicon, glass, polystyrene, aluminium, steel, iron, copper, nickel, silver, or gold. Nitrocellulose as well as plastics such as nylon, which can exist in the form of pellets or also as resin matrices, may also be used. An overview of the Prior Art in oligomer array manufacturing can be gathered from a special edition of Nature Genetics (*Nature Genetics Supplement*, Volume 21, January 1999, and from the literature cited therein). Fluorescently labelled probes are often used for the scanning of immobilized DNA arrays. The simple attachment of Cy3 and Cy5 dyes to the 5'-OH of the specific probe are particularly suitable for fluorescence labels. The detection of the fluorescence of the hybridised probes may be carried out, for example, via a confocal microscope. Cy3 and Cy5 dyes, besides many others, are commercially available.

It is also anticipated that the oligonucleotides, or particular sequences thereof, may constitute all or part of an "virtual array" wherein the oligonucleotides, or particular sequences thereof, are used, for example, as 'specifiers' as part of, or in combination with a diverse population of unique labeled probes to analyze a complex mixture of analytes. Such a method, for example is described in US 2003/0013091 (U.S. Ser. No. 09/898,743, published 16 Jan. 2003). In such methods, enough labels are generated so that each nucleic acid in the complex mixture (i.e., each analyte) can be uniquely bound by a unique label and thus detected (each label is directly counted, resulting in a digital read-out of each molecular species in the mixture).

It is particularly preferred that the oligomers according to the invention are utilised for determining the prognosis of a subject having cell proliferative disorder, preferably cancer. It is further particularly preferred that the oligomers according to the invention are utilised for determining the prognosis of said subject subsequent to a therapy comprising at least one anthracycline.

Kits

Moreover, an additional aspect of the present invention is a kit comprising: a means for determining methylation of at least one gene selected from the group consisting of CDO1; APC; BMPR1A; CTAGE5; CXCL12; NCR1; NFATC2; PAX9; POU4F3; and ZBTB16. The means for determining methylation of at least one gene selected from the group consisting of CDO1; APC; BMPR1A; CTAGE5; CXCL12; NCR1; NFATC2; PAX9; POU4F3; and ZBTB16 comprise preferably a bisulfite-containing reagent; one or a plurality of oligonucleotides consisting whose sequences in each case are identical, are complementary, or hybridise under stringent or highly stringent conditions to an at least 9 or more preferably 18 base long segment of a sequence selected from SEQ ID NO: 21-40 and 61-80 or preferred regions thereof according to SEQ ID NO: 41-60 and 81-100; and optionally instructions for carrying out and evaluating the described method of methylation analysis. In one embodiment the base sequence of said oligonucleotides comprises at least one CpG, CpA or TpG dinucleotide.

In a further embodiment, said kit may further comprise standard reagents for performing a CpG position-specific methylation analysis, wherein said analysis comprises one or more of the following techniques: MS-SNuPE, MSP, MethyLight™, HeavyMethyl, COBRA, and nucleic acid sequencing. However, a kit along the lines of the present invention can also contain only part of the aforementioned components.

In a preferred embodiment the kit may comprise additional bisulfite conversion reagents selected from the group consisting of: DNA denaturation buffer; sulfonation buffer; DNA recovery reagents or kits (e.g., precipitation, ultrafiltration, affinity column); desulfonation buffer; and DNA recovery components.

In a further alternative embodiment, the kit may contain, packaged in separate containers, a polymerase and a reaction buffer optimised for primer extension mediated by the polymerase, such as PCR. In another embodiment of the invention the kit further comprising means for obtaining and/or storing a biological sample of the subject. Preferred is a kit, which further comprises a container suitable for containing the means for determining methylation of at least one gene selected from the group consisting of CDO1; APC; BMPR1A; CTAGE5; CXCL12; NCR1; NFATC2; PAX9; POU4F3; and ZBTB16 in the biological sample of the subject, and most preferably further comprises instructions for use and interpretation of the kit results. In a preferred embodiment the kit comprises: (a) a bisulfite reagent; (b) a container suitable for containing the said bisulfite reagent and the biological sample of the subject; (c) at least one set of primer oligonucleotides containing two oligonucleotides whose sequences in each case are identical, are complementary, or hybridise under stringent or highly stringent conditions to an at least 9 or more preferably 18 base long segment of a sequence selected from SEQ ID NO: 21-40 and 61-80 or preferred regions thereof according to SEQ ID NO: 41-60 and 81-100; and optionally (d) instructions for use and interpretation of the kit results. In an alternative preferred embodiment the kit comprises: (a) a bisulfite reagent; (b) a container suitable for containing the said bisulfite reagent and the biological sample of the subject; (c) at least one oligonucleotides and/or PNA-oligomer having a length of at least 9 or 16 nucleotides which is identical to or hybridises to a pre-treated nucleic acid sequence according to one of SEQ ID NO: 21-40 and 61-80 or preferred regions thereof according to SEQ ID NO: 41-60 and 81-100 and sequences complementary thereto; and optionally (d) instructions for use and interpretation of the kit results.

In an alternative embodiment the kit comprises: (a) a bisulfite reagent; (b) a container suitable for containing the said bisulfite reagent and the biological sample of the subject; (c) at least one set of primer oligonucleotides containing two oligonucleotides whose sequences in each case are identical, are complementary, or hybridise under stringent or highly stringent conditions to an at least 9 or more preferably 18 base long segment of a sequence selected from SEQ ID NO: 21-40 and 61-80 or preferred regions thereof according to SEQ ID NO: 41-60 and 81-100; (d) at least one oligonucleotides and/or PNA-oligomer having a length of at least 9 or 16 nucleotides which is identical to or hybridises to a pre-treated nucleic acid sequence according to one of SEQ ID NO: 21-40 and 61-80 or preferred regions thereof according to SEQ ID NO: 41-60 and 81-100 and sequences complementary thereto; and optionally (e) instructions for use and interpretation of the kit results.

The kit may also contain other components such as buffers or solutions suitable for blocking, washing or coating, packaged in a separate container.

Another aspect of the invention relates to a kit for use in determining the prognosis of a subject having cell proliferative disorder, preferably cancer, said kit comprising: a means for measuring the level of transcription of at least one gene selected from the group consisting of CDO1; APC; BMPR1A; CTAGE5; CXCL12; NCR1; NFATC2; PAX9;

POU4F3; and ZBTB16 and a means for determining methylation of at least one gene selected from the group consisting of CDO1; APC; BMPR1A; CTAGE5; CXCL12; NCR1; NFATC2; PAX9; POU4F3; and ZBTB16. Said kit is particularly suited to determining prognosis of a subject subsequent to a therapy comprising at least one anthracycline.

Typical reagents (e.g., as might be found in a typical COBRA™-based kit) for COBRA™ analysis may include, but are not limited to: PCR primers for at least one gene selected from the group consisting of CDO1; APC; BMPR1A; CTAGE5; CXCL12; NCR1; NFATC2; PAX9; POU4F3; and ZBTB16 restriction enzyme and appropriate buffer; gene-hybridization oligonucleotide; control hybridization oligonucleotide; kinase labeling kit for oligonucleotide probe; and labeled nucleotides. Typical reagents (e.g., as might be found in a typical MethyLight™-based kit) for MethyLight™ analysis may include, but are not limited to: PCR primers for the bisulfite converted sequence of at least one gene selected from the group consisting of CDO1; APC; BMPR1A; CTAGE5; CXCL12; NCR1; NFATC2; PAX9; POU4F3; and ZBTB16 bisulfite specific probes (e.g. Taq-Man™ or LightCycler™); optimized PCR buffers and deoxynucleotides; and Taq polymerase.

Typical reagents (e.g., as might be found in a typical Ms-SNuPE™-based kit) for MsSNuPE™ analysis may include, but are not limited to: PCR primers for specific gene (or bisulfite treated DNA sequence or CpG island); optimized PCR buffers and deoxynucleotides; gel extraction kit; positive control primers; Ms-SNuPE™ primers for the bisulfite converted sequence of at least one gene selected from the group consisting of CDO1; APC; BMPR1A; CTAGE5; CXCL12; NCR1; NFATC2; PAX9; POU4F3; and ZBTB16 reaction buffer (for the Ms-SNuPE reaction); and labeled nucleotides.

Typical reagents (e.g., as might be found in a typical MSP-based kit) for MSP analysis may include, but are not limited to: methylated and unmethylated PCR primers for the bisulfite converted sequence of at least one gene selected from the group consisting of CDO1; APC; BMPR1A; CTAGE5; CXCL12; NCR1; NFATC2; PAX9; POU4F3; and ZBTB16, optimized PCR buffers and deoxynucleotides, and specific probes.

Moreover, an additional aspect of the present invention is an alternative kit comprising a means for determining at least one gene selected from the group consisting of CDO1; APC; BMPR1A; CTAGE5; CXCL12; NCR1; NFATC2; PAX9; POU4F3; and ZBTB16 methylation, wherein said means comprise preferably at least one methylation specific restriction enzyme; one or a plurality of primer oligonucleotides (preferably one or a plurality of primer pairs) suitable for the amplification of a sequence comprising at least one CpG dinucleotide of a sequence selected from SEQ ID NO: 1-10, or preferred regions thereof according to SEQ ID NO: 11-20; and optionally instructions for carrying out and evaluating the described method of methylation analysis. In one embodiment the base sequence of said oligonucleotides are identical, are complementary, or hybridise under stringent or highly stringent conditions to an at least 18 base long segment of a sequence selected from SEQ ID NO: 1-10, or preferred regions thereof according to SEQ ID NO: 11-20.

In a further embodiment said kit may comprise one or a plurality of oligonucleotide probes for the analysis of the digest fragments, preferably said oligonucleotides are identical, are complementary, or hybridise under stringent or highly stringent conditions to an at least 16 base long segment of a sequence selected from SEQ ID NO: 1-10, or preferred regions thereof according to SEQ ID NO: 11-20.

In a preferred embodiment the kit may comprise additional reagents selected from the group consisting: buffer (e.g. restriction enzyme, PCR, storage or washing buffers); DNA recovery reagents or kits (e.g., precipitation, ultrafiltration, affinity column) and DNA recovery components.

In a further alternative embodiment, the kit may contain, packaged in separate containers, a polymerase and a reaction buffer optimized for primer extension mediated by the polymerase, such as PCR. In another embodiment of the invention the kit further comprising means for obtaining and/or storing a biological sample of the subject. In a preferred embodiment the kit comprises: (a) a methylation sensitive restriction enzyme reagent; (b) a container suitable for containing the said reagent and the biological sample of the subject; (c) at least one set of oligonucleotides one or a plurality of nucleic acids or peptide nucleic acids which are identical, are complementary, or hybridize under stringent or highly stringent conditions to an at least 9 base long segment of a sequence selected from SEQ ID NO: 1-10, or preferred regions thereof according to SEQ ID NO: 11-20; and optionally (d) instructions for use and interpretation of the kit results.

In an alternative preferred embodiment the kit comprises: (a) a methylation sensitive restriction enzyme reagent; (b) a container suitable for containing the said reagent and the biological sample of the subject; (c) at least one set of primer oligonucleotides suitable for the amplification of a sequence comprising at least one CpG dinucleotide of a sequence selected from SEQ ID NO: 1-10, or preferred regions thereof according to SEQ ID NO: 11-20; and optionally (d) instructions for use and interpretation of the kit results.

In an alternative embodiment the kit comprises: (a) a methylation sensitive restriction enzyme reagent; (b) a container suitable for containing the said reagent and the biological sample of the subject; (c) at least one set of primer oligonucleotides suitable for the amplification of a sequence comprising at least one CpG dinucleotide of a sequence selected from SEQ ID NO: 1-10, or preferred regions thereof according to SEQ ID NO: 11-20; (d) at least one set of oligonucleotides one or a plurality of nucleic acids or peptide nucleic acids which are identical, are complementary, or hybridize under stringent or highly stringent conditions to an at least 9 base long segment of a sequence selected from SEQ ID NO: 1-10, or preferred regions thereof according to SEQ ID NO: 11-20 and optionally (e) instructions for use and interpretation of the kit results.

The kit may also contain other components such as buffers or solutions suitable for blocking, washing or coating, packaged in a separate container.

The invention further relates to a kit for use in determining the prognosis of a subject having cell proliferative disorder, preferably cancer, in a subject by means of methylation-sensitive restriction enzyme analysis. Said kit comprises a container and a DNA microarray component. Said kit is particularly suited to determining subject prognosis subsequent to a therapy comprising at least one anthracycline. Said DNA microarray component being a surface upon which a plurality of oligonucleotides are immobilized at designated positions and wherein the oligonucleotide comprises at least one CpG methylation site. At least one of said oligonucleotides is specific for at least one gene selected from the group consisting of CDO1; APC; BMPR1A; CTAGE5; CXCL12; NCR1; NFATC2; PAX9; POU4F3; and ZBTB16 and comprises a sequence of at least 15 base pairs in length but no more than 200 bp of a sequence according to one of SEQ ID NO: 1-10, or preferred regions thereof according to SEQ ID NO: 11-20. Preferably said sequence is at least 15 base pairs in length but no more than 80 bp of a sequence according to one of SEQ ID NO: 1-10, or preferred regions thereof according to SEQ ID NO: 11-20. It is further preferred that said sequence is at least 20 base pairs in length but no more than 30 bp of a sequence according to one of SEQ ID NO: 1-10, or preferred regions thereof according to SEQ ID NO: 11-20.

Said test kit preferably further comprises a restriction enzyme component comprising one or a plurality of methylation-sensitive restriction enzymes.

In a further embodiment said test kit is further characterized in that it comprises at least one methylation-specific restriction enzyme, and wherein the oligonucleotides comprise a restriction site of said at least one methylation specific restriction enzymes.

The kit may further comprise one or several of the following components, which are known in the art for DNA enrichment: a protein component, said protein binding selectively to methyllated DNA; a triplex-forming nucleic acid component, one or a plurality of linkers, optionally in a suitable solution; substances or solutions for performing a ligation e.g. ligases, buffers; substances or solutions for performing a column chromatography; substances or solutions for performing an immunology based enrichment (e.g. immunoprecipitation); substances or solutions for performing a nucleic acid amplification e.g. PCR; a dye or several dyes, if applicable with a coupling reagent, if applicable in a solution; substances or solutions for performing a hybridization; and/or substances or solutions for performing a washing step.

The described invention further provides a composition of matter useful for determining the prognosis of a subject having cell proliferative disorder, preferably cancer. Said composition of matter is particularly suited to determining said prognosis subsequent to a therapy comprising at least one anthracycline.

Said composition comprising at least one nucleic acid 18 base pairs in length of a segment of the nucleic acid sequence disclosed in SEQ ID NO: 21-40 and 61-80 or preferred regions thereof according to SEQ ID NO: 41-60 and 81-100, and one or more substances taken from the group comprising: 1-5 mM Magnesium Chloride, 100-500 µM dNTP, 0.5-5 units of taq polymerase, bovine serum albumen, an oligomer in particular an oligonucleotide or peptide nucleic acid (PNA)-oligomer, said oligomer comprising in each case at least one base sequence having a length of at least 9 nucleotides which is complementary to, or hybridizes under moderately stringent or stringent conditions to a pretreated genomic DNA according to one of the SEQ ID NO: 21-40 and 61-80 or preferred regions thereof according to SEQ ID NO: 41-60 and 81-100 and sequences complementary thereto. It is preferred that said composition of matter comprises a buffer solution appropriate for the stabilization of said nucleic acid in an aqueous solution and enabling polymerase based reactions within said solution. Suitable buffers are known in the art and commercially available.

In further preferred embodiments of the invention said at least one nucleic acid is at least 50, 100, 150, 200, 250 or 500 base pairs in length of a segment of the nucleic acid sequence disclosed in SEQ ID NO: 21-40 and 61-80 or preferred regions thereof according to SEQ ID NO: 41-60 and 81-100.

TABLE 1

Genomic sequences and treated variants thereof according to the invention.

| Gene | Genomic SEQ ID NO: | Pretreated methylated sequence (sense) SEQ ID NO: | Pretreated methylated strand (antisense) SEQ ID NO: | Pretreated unmethylated sequence (sense) SEQ ID NO: | Pretreated unmethylated sequence (antisense) SEQ ID NO: |
|---|---|---|---|---|---|
| APC | 1 | 21 | 22 | 61 | 62 |
| BMPR1A | 2 | 23 | 24 | 63 | 64 |
| CDO1 | 3 | 25 | 26 | 65 | 66 |
| CTAGE5 | 4 | 27 | 28 | 67 | 68 |
| CXCL12 | 5 | 29 | 30 | 69 | 70 |
| NCR1 | 6 | 31 | 32 | 71 | 72 |
| NFATC2 | 7 | 33 | 34 | 73 | 74 |
| PAX9 | 8 | 35 | 36 | 75 | 76 |
| POU4F3 | 9 | 37 | 38 | 77 | 78 |
| ZBTB16 | 10 | 39 | 40 | 79 | 80 |

TABLE 2

Particularly preferred regions of the sequences according to table 1.

| Gene | Genomic SEQ ID NO: | Pretreated methylated sequence (sense) SEQ ID NO: | Pretreated methylated strand (antisense) SEQ ID NO: | Pretreated unmethylated sequence (sense) SEQ ID NO: | Pretreated unmethylated sequence (antisense) SEQ ID NO: |
|---|---|---|---|---|---|
| APC | 11 | 41 | 42 | 81 | 82 |
| BMPR1A | 12 | 43 | 44 | 83 | 84 |
| CDO1 | 13 | 45 | 46 | 85 | 86 |
| CTAGE5 | 14 | 47 | 48 | 87 | 88 |
| CXCL12 | 15 | 49 | 50 | 89 | 90 |
| NCR1 | 16 | 51 | 52 | 91 | 92 |
| NFATC2 | 17 | 53 | 54 | 93 | 94 |
| PAX9 | 18 | 55 | 56 | 95 | 96 |
| POU4F3 | 19 | 57 | 58 | 97 | 98 |
| ZBTB16 | 20 | 59 | 60 | 99 | 100 |

EXAMPLE

1. Abstract

Figure 1:
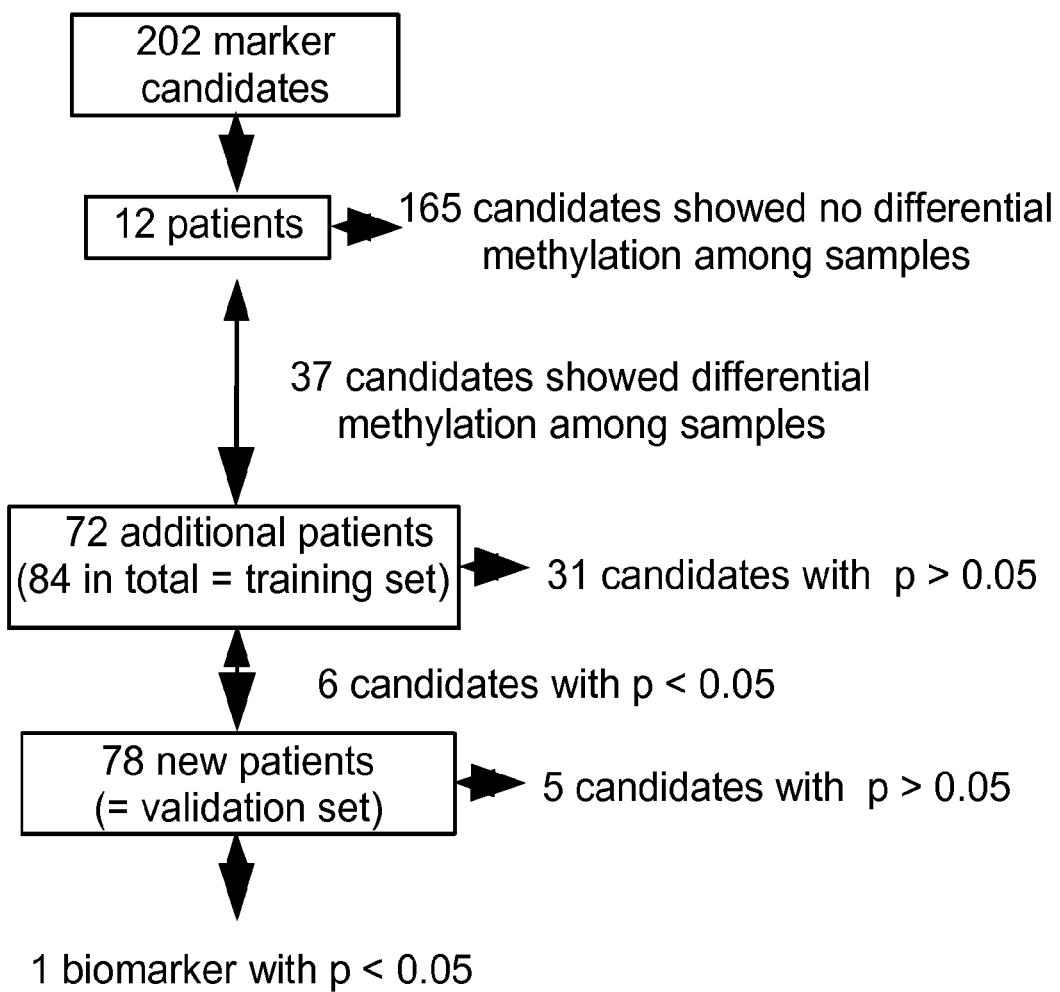
FIG. 1 shows an overview of the marker candidate selection procedure according to paragraph 3 of the example.

Various biomarkers for prediction of distant metastasis in lymph node-negative breast cancer have been described, however, there is still a great demand for predictive biomarkers for patients with lymph node-positive (LNP) disease in the context of distinct systemic therapies. DNA methylation is aberrant in breast cancer and is likely to play a major role in disease progression. In this study, the DNA methylation status of 202 candidate loci was screened to identify those loci that may predict outcome in LNP/estrogen receptor-positive (ER+) breast cancer patients with adjuvant anthracycline-based chemotherapy.

Quantitative bisulfite sequencing was used to analyze DNA methylation biomarker candidates in a retrospective cohort of 162 LNP/ER+ breast cancer patients, who received adjuvant anthracycline-based chemotherapy. First, twelve breast cancer specimens were analyzed for all 202 candidate loci to exclude genes that showed no differential methylation. To identify genes that predict distant metastasis, the remaining loci were analyzed in 84 selected cases, including the 12 initial ones. Significant loci were analyzed in the remaining 78 independent cases. Metastasis-free survival analysis was conducted by using Cox regression, time-dependent ROC analysis, and the Kaplan-Meier method. Pairwise multivariate regression analysis was performed by linear Cox Proportional Hazard models, testing the association between methylation scores and clinical parameters with respect to metastasis-free survival.

Of the 202 loci analysed, 37 showed some indication of differential DNA methylation among the initial 12 patient samples tested. Of those, 6 loci were associated with outcome in the initial cohort (n=84, log rank test, p<0.05).

Promoter DNA methylation of cysteine dioxygenase 1 (CDO1) was confirmed in univariate and in pairwise multivariate analysis adjusting for age at surgery, pathological T stage, progesterone receptor status, grade, and endocrine therapy as a strong and independent biomarker for outcome prediction in the independent validation set (log rank test p-value=0.0010).

CDO1 methylation was shown to be a strong predictor for distant metastasis in retrospective cohorts of LNP/ER+ breast cancer patients, who had received adjuvant anthracycline-based chemotherapy.

2. Introduction

Breast cancer is the most frequent cancer in women (23% of all cancers), ranking second overall when both sexes are considered together. Chemotherapy of breast cancer has progressed substantially over the past decades. Anthracyclines, introduced in the 1980s, are among the most potent agents for treatment of breast cancer and thus are components of many (neo)-adjuvant and palliative regimens, more recently often in combination with taxanes.

In node-positive breast cancer, anthracycline-based adjuvant chemotherapy has become the standard of care since the 1990s; 69% of LNP breast cancer patients remained disease-free after five years after treatment with anthracycline-based chemotherapy. Those long-term disease-free patients are supposed to have been effectively treated and any more aggressive treatment thus seems to be unnecessary. Yet, treatment with anthracyclines is linked with both, acute and long-term side effects, most notably cardiotoxicity. Therefore, if a biomarker were available to reliably identify LNP patients with a low risk of recurrence after adjuvant anthracycline-based chemotherapy, further treatment of this patient group with other potentially chemotherapy agents with differential toxicity patterns may be avoided. Predictive biomarkers for response to anthracyclines are therefore highly essential and could help individualize decisions regarding whether to incorporate anthracyclines into adjuvant therapy regimens for individual patients.

DNA methylation plays an important role in fundamental biological processes such as development and cellular differentiation. The same applies to carcinogenesis and cancer progression, suggesting that DNA methylation analysis may be a valuable source of predictive and/or prognostic biomarkers. In this study, quantitative bisulfite sequencing was used to screen 202 biomarker candidates for their prognostic impact in LNP/ER+ breast cancer patients who had received adjuvant anthracycline-based chemotherapy. The marker candidates were selected from the literature or identified by differential methylation hybridization (DMH) technology, a method for genome-wide discovery of methylation biomarkers. Promoter DNA methylation of cysteine dioxygenase 1 (CDO1) was identified as a strong predictor of distant metastasis. This finding was confirmed in an independent patient group of advanced LNP/ER+ breast cancer patients treated with adjuvant anthracycline-based chemotherapy.

3. Methods 3.1 Patients

The study cohort was comprised of 162 breast cancer patients whose tumor samples were obtained from 4 clinical centers: Erasmus Medical Center, Rotterdam, The Netherlands; Centre Rene Huguenin, St. Cloud, France; Stiftung Tumorbank Basel, Basel, Switzerland; and Department of Obstetrics and Gynecology, Technical University of Munich, Germany. Appropriate consent, according to institutional requirements, was obtained for all patients. The study protocol was approved by the local ethics committees. Patient characteristics are shown in table 3. All breast cancer patients were anthracycline-treated with estrogen receptor-positive, lymph node-positive tumors.

3.2 DNA Preparation

Snap-frozen tumor tissue or tumor cell nuclei pelleted at 100,000 g were used to obtain genomic DNA as previously described. Genomic DNA was extracted using the QIAamp DNA Mini Kit (Qiagen, Hilden, Germany), following the manufacturer's instructions (tissue protocol). The DNA concentration was quantified by UV spectrophotometry using a Nanodrop® ND-1000 spectral photometer (Nanodrop Technologies, DE, USA). Artificially methylated DNA (CpGenome™ Universal Methylated DNA, Millipore, Mass., USA) was used as completely methylated reference DNA.

3.3 Bisulfite Conversion

Two µg of extracted DNA was bisulfite converted using the EpiTect® Kit (Qiagen, Hilden, Germany) according to the manufacturer's recommendations with the exception that no carrier RNA was used. DNA concentration was quantified via UV spectrophotometry as described above.

3.4 PCR Amplification

PCR amplification was done in a 25 µl volume (1 U HotStar Taq polymerase [Qiagen, Hilden, Germany], 1×PCR buffer [Qiagen, Hilden, Germany], 0.2 mM each dNTP [Fermentas, Burlington, Canada], 0.5 µM both primers [MWG-Biotech, Ebersberg, Germany], and 20 ng template DNA). Incubation was done using the following temperature profile: 15 min/95° C. and 45 cycles with 20 s/95° C., 45 s/58° C. and 30 s/72° C. The primer sequences and the sequences of the respective target loci (prior to bisulfite conversion) are listed in table 6. Each reverse primer contained the sequence CGTCGTCG at its 5' end.

3.5. Sequencing and Raw Data Processing

Quantitative bisulfite sequencing was carried out as previously described. ABI sequencing electropherograms were converted to text files using BioEdit 6.0.7 software and imported into Microsoft Excel. The trace containing the methylation information was visualized and the normalization signal identified. The electropherograms were shifted until the normalization signal of each sample was located at the same position. The normalization signal was integrated and each data point of the electropherogram divided by this normalization value. The analyzed PCR fragments contained several CpG sites. The signals of the single CpG sites of completely methylated DNA were used to identify the CpG positions in the electropherograms of the patient samples. The maximum intensity of a specific CpG site was defined as the maximum in the region ±30 data points referred to the respective peak in the reference trace of the completely methylated DNA. The averaged intensities of all CpG sites from one PCR fragment were used as measurement (methylation score) for statistical analysis.

3.6. Statistical Analysis

Time-dependent ROC curves for censored survival data and the resulting AUC were calculated according to Heagerty et al. WinSTAT for Microsoft Excel (www.winstat.com) was used for Kaplan-Meier survival analysis and log rank test. The median methylation value in the respective patient group was used as the cut point for dichotomization.

The relation between time to distant metastasis and DNA methylation score was analyzed by a linear univariate Cox Proportional Hazard model. Likelihood ratio tests were performed to test for a significant impact of DNA methylation score for the CDO1 amplificate on clinical end points. Hazard Ratios for continuous variables were calculated. Pairwise multivariate regression analysis, testing the association between clinical end point and DNA methylation score and/or clinical parameters, was performed by employing linear Cox Proportional Hazard models.

4. Results

A recently published novel method for quantitative bisulfite sequencing [12] was used to analyze the methylation status of 202 potential DNA methylation biomarkers in tumors from 162 anthracycline-treated, estrogen receptor-positive, lymph node-positive breast cancer patients in order to evaluate their potential to predict distant metastasis. The marker candidates were taken from the literature or have previously been identified using differential methylation hybridization (DMH), a genome-wide discovery method (data not shown). A consecutive marker selection procedure as depicted in FIG. 1 was developed in order to efficiently identify DNA methylation biomarkers for outcome prediction. In a first selection step, all 202 loci were analyzed using bisulfite treated DNA from 12 randomly selected individual tumors to exclude those that showed no evidence of differential methylation among the samples. The remaining candidates were further tested for their potential ability to predict distant metastasis in a set of 72 additional patient specimens, resulting in a training group of 84 patients in total. In the final step of analysis, the significant DNA methylation biomarkers evolving from the training set were further analyzed in an independent validation set of DNA samples from 78 patients, in order to confirm and validate their true clinical potential. The characteristics of patients belonging to the training and validation sets are shown in table 3.

Figure 2:
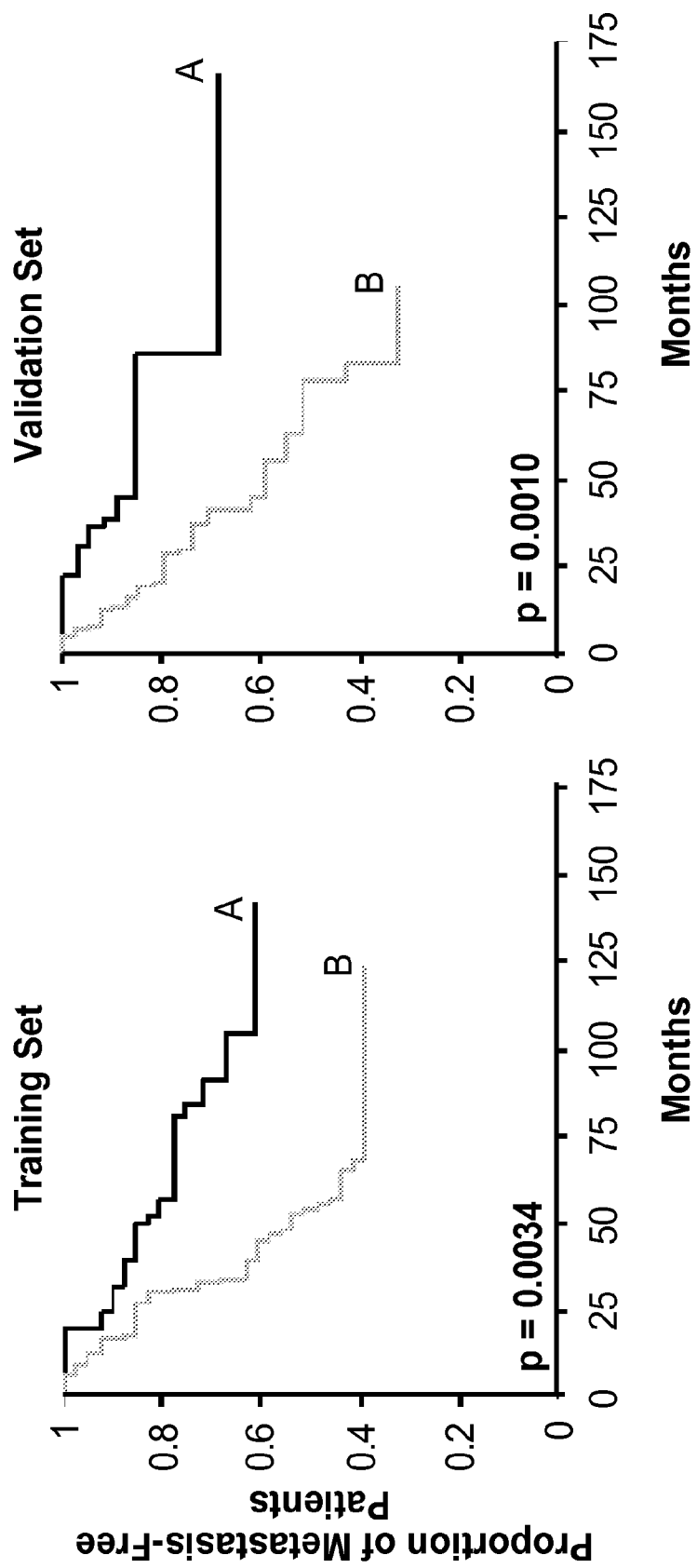
FIG. 2 shows a Kaplan-Meier analysis according to example 3. Indicated is the metastasis-free survival in the training set (84 patients) and the validation set (78 patients) of lymph node-positive patients with estrogen receptor-positive tumors, adjuvantly treated with anthracycline and stratified by the DNA methylation status of CDO1. Median CDO1 methylation of the respective population was used as the cut point according to paragraph 3.6. of the example. Curves labeled with A represent patients with hypomethylated CDO1, while curves labeled with B indicate for patients with hypermethylated CDO1.

From the initially analyzed 202 loci, 165 did not show an apparent differential DNA methylation pattern among the initial 12 samples tested, and therefore these loci were excluded from further analyses. Of the remaining 37 candidates, six loci were associated with the occurrence of distant metastasis in this training population. Time-dependent ROC analysis and Kaplan-Meier analysis was performed. In order to avoid an overly optimistic result, the median DNA methylation score of the training set was used as the cut point. The results of the DNA methylation biomarkers showing potential impact in the training set are shown in table 4. Six genes (CDO1, APC, ZBTB16, NCR1, POU4F3, and CXCL12) emerged as potential biomarkers in the training set indicated by p<0.05 and AUC >0.6. Analysis of the six genes in the validation set (table 4) confirmed the ability of the CDO1 gene to predict outcome (p=0.0010, AUC=0.69) while the predictive ability of DNA methylation of the other five genes could not be confirmed in the validation set. The Kaplan-Meier survival plots stratified by the DNA methylation status of CDO1 both in the training and validation set are depicted in FIG. 2. Evidently, DNA methylation of CDO1 is a strong biomarker to predict distant metastasis in LNP patients with ER+tumors treated with adjuvant anthracycline containing therapy. Table 5 shows the results of the univariate and the pairwise multivariate Cox Proportional Hazard models of the validation population (n=78). In univariate analysis, the DNA methylation score for CDO1 is associated with a high risk of distant recurrence in this patient group (p=0.0098, HR=3.7, 95% CI 1.4-9.8). In addition, progesterone receptor status (p=0.0190, HR=2.7, 95% CI 1.2-6.0) was significantly associated with time-to-distant metastasis in this group whereas tumor stage, endocrine treatment, tumor grade, and age at surgery were not. CDO1 DNA methylation was a significant marker in the pairwise multivariate analysis including age at surgery, pathological T stage, progesterone receptor status, tumor grade or endocrine therapy. Patients who suffered disease recurrence showed higher DNA methylation of the CDO1 locus than those surviving metastasis-free.

5. Conclusion

DNA methylation of 202 loci was analyzed in tumors from breast cancer patients who were estrogen receptor-positive, lymph node-positive, and treated with adjuvant anthracycline-based chemotherapy, in order to identify biomarkers to predict patient outcome. A stepwise biomarker selection strategy was developed which allowed for optimization of experimental efforts and costs for large scale analysis of genes. In a first selection step, a selected small number of DNA samples were analyzed in order to separate out loci which showed no evidence of differential DNA methylation. The remaining 37 loci were further analyzed in a training set in order to identify loci with a potential to predict patient outcome. Subsequently, the biomarker performance of the most promising loci was tested in another set of DNAs derived from tumor tissues of an independent group of patients. This procedure led to the identification of cysteine dioxygenase 1 (CDO1) as a strong DNA methylation biomarker for outcome prediction in the analyzed patient group.

CDO1 was identified as a candidate biomarker using the DMH method by determining its DNA methylation status in tumors from patients with metastatic breast cancer who were treated by FAC (5-fluorouracil, adriamycine, and cyclophosphamide) regimen as first-line therapy. The CDO1 gene encodes for an enzyme that converts cysteine to cysteine sulphinic acid and is the rate-limiting step in sulphate production. CDO1 is understood to be one of the key enzymes in the taurine biosynthetic pathway. Taurine inhibits apoptosis. The human CDO1 gene is located at chromosome 5q23.2 and is homologous to the rat and murine cysteine dioxigenases. Murine Cdo1 may be involved in the regulation of protein function and antioxidant defense mechanisms through its ability to oxidize cysteine residues. As has been previously assumed, the deletion or epigenetic silencing of the chromosomal region where CDO1 is located is a frequent mechanism contributing to colorectal tumorigenesis. Recently, over-expression of CDO1 was described for the Sezary syndrome, an aggressive cutaneous T-cell lymphoma.

Nonetheless, as of today, no aberrant DNA methylation of the CDO1 gene has been described in the context of breast cancer. Expression of cysteine dioxygenase was found in ductal cells of pregnant rats, but not in other mammary epithelial cells or in ductal cells of nonpregnant rats. Interestingly, repression of Cdo1 expression was identified to be associated with the malignant transition from mammary intraepithelial neoplasia to tumors in an engineered mouse-based model of ductal carcinoma in situ.

However, in the present study, DNA methylation of CDO1 was found to be a strong biomarker for prediction of distant recurrence in lymph node-positive patients with estrogen receptor-positive tumors treated with adjuvant anthracycline containing therapy.

6. Abbreviations
ROC Receiver Operating Characteristic
AUC Area under the Curve
DMH Differential Methylation Hybridization
CI Confidence Interval
HR Hazard Ratio
CDO1 Cysteine Dioxygenase 1
APC Adenomatosis Polyposis Coli
MDA Multiple Displacement Amplification
NCR1 Natural Cytotoxicity Triggering Receptor 1
POU4F3 POU Class 4 Homeobox 3
CXCL12 Chemokine (C—X—C motif) Ligand 12
ZBTB16 Zinc Finger and BTB Domain Containing 16

TABLE 3

Characteristics of the 162 estrogen receptor-positive and lymph node positive breast cancer patients treated with anthracyclines.

|  | Training Set[†] | | Validation Set | |
| --- | --- | --- | --- | --- |
|  | All | Distant Metastasis | All | Distant Metastasis |
| Total Number of Patients | 84 (100%) | 39 | 78 (100%) | 25 |
| Follow-up | | | | |
| Median follow-up [Months] | 80 | | 53.5 | |
| Range [Months] | 6-144 | | 5-166 | |
| Age at Diagnosis | | | | |
| ≤50 Years | 38 (45%) | 20 | 41 (53%) | 16 |
| >50 Years | 46 (55%) | 19 | 37 (47%) | 19 |
| Median Age (Years) | 49 | | 49 | |
| Range (Years) | 29-71 | | 33-81 | |
| T stage | | | | |
| ≤2 cm (T1) | 19 (23%) | 4 | 24 (31%) | 5 |
| >2 cm (T2 + T3) | 63 (75%) | 35 | 53 (68%) | 19 |
| Unknown | 2 (2%) | 0 | 1 (1%) | 1 |
| Tumor Grade | | | | |
| G1 | 2 (2%) | 0 | 3 (4%) | 1 |
| G2 | 24 (29%) | 11 | 30 (38%) | 7 |
| G3 | 47 (56%) | 21 | 28 (36%) | 11 |
| Unknown | 11 (13%) | 7 | 17 (22%) | 6 |
| Estrogen Receptor Status | | | | |
| Negative | 0 | 0 | 0 | 0 |
| Positive | 84 (100%) | 39 | 78 (100%) | 25 |
| Progesterone Receptor Status | | | | |
| Negative | 12 (14%) | 4 | 18 (23%) | 9 |
| Positive | 72 (86%) | 35 | 60 (77%) | 16 |
| Endocrine Treatment | | | | |
| Yes | 22 (26%) | 8 | 37 (47%) | 9 |
| No | 61 (73%) | 30 | 40 (51%) | 15 |
| Unknown | 1 (1%) | 1 | 1 (1%) | 1 |

[†]The training set was enriched for specimens that lack PITX2 methylation.

TABLE 4

Time-dependent ROC analysis of the candidate genes in the training and validation set of LNP patients with ER + tumors treated with adjuvant anthracycline containing therapy.

| Gene | Training Set (n = 84) | | Validation Set (n = 78) | |
| --- | --- | --- | --- | --- |
|  | AUC[†] | p-value[‡] | AUC[†] | p-value[‡] |
| CDO1 | 0.70 | 0.0034 | 0.69 | 0.0010 |
| APC | 0.68 | 0.0204 | 0.55 | 0.5306 |
| ZBTB16 | 0.67 | 0.0224 | 0.63 | 0.0582 |
| NCR1 | 0.63 | 0.0239 | 0.56 | 0.9048 |
| POU4F3 | 0.69 | 0.0248 | 0.69 | 0.0754 |
| CXCL12 | 0.67 | 0.0282 | 0.49 | 0.4854 |

[†]Shown are the AUC of the ROC at 48 months after surgery
[‡]The p-values are those obtained by the log rank test in Kaplan-Meier survival analysis and the genes are ranked according these p-values. The median DNA methylation score was used as the cut point.

TABLE 5

Univariate and pairwise multivariate Cox Proportional Hazards analysis for time-to-distant metastasis.

| | Number of samples | Hazard Ratio (95% CI) | p-value[‡] |
| --- | --- | --- | --- |
| Univariate Analysis[†] | | | |
| CDO1 DNA Methylation | 78 | 3.7 (1.4-9.8) | 0.0098 |
| Age at Surgery | 78 | 1.3 (0.6-2.8) | 0.5545 |
| Tumor Stage (T2, T3 vs. T1) | 78 | 2.0 (0.7-5.2) | 0.1799 |
| Progesterone Receptor Status (Positive vs. Negative) | 77 | 2.7 (1.2-6.0) | 0.0190 |
| Endocrine Treatment (No vs. Yes) | 77 | 2.0 (0.9-4.5) | 0.1115 |
| Tumor Grade (1, 2 vs. 3) | 61 | 2.0 (0.8-4.9) | 0.1397 |
| Pairwise Multivariate Analysis[†] | | | |
| CDO1 DNA Methylation | 78 | 3.9 (1.5-10.5) | 0.0072 |
| Age at Surgery | 78 | 1.5 (0.7-3.4) | 0.3160 |
| CDO1 DNA Methylation | 77 | 3.5 (1.3-9.5) | 0.0128 |
| T Stage (T2, T3 vs. T1) | 77 | 2.0 (0.7-5.3) | 0.1790 |
| CDO1 DNA Methylation | 78 | 3.5 (1.3-9.4) | 0.0123 |
| Progesterone Receptor Status (Positive vs. Negative) | 78 | 2.5 (1.1-5.7) | 0.0275 |
| CDO1 DNA Methylation | 77 | 4.6 (1.6-13.5) | 0.0055 |
| Endocrine Treatment (No vs. Yes) | 77 | 2.0 (0.9-4.7) | 0.0938 |
| CDO1 DNA Methylation | 61 | 3.1 (1.1-8.7) | 0.0318 |
| Tumor Grade (1, 2 vs. 3) | 61 | 1.7 (0.7-4.3) | 0.2506 |

[†]CDO1 DNA methylation and age at surgery were analyzed as continuous variables. T stage, endocrine treatment and progesterone receptor status were analyzed as binary variables.
[‡]p-values refer to Likelihood-ratio test.

TABLE 6

Primer sequence numbers and sequence numbers of the respective target loci (prior to bisulfite conversion).

| Gene | Primer Forward | Primer Reverse | PCR product |
| --- | --- | --- | --- |
| APC | SEQ ID NO: 101 | SEQ ID NO: 102 | SEQ ID NO: 103 |
| CDO1 | SEQ ID NO: 104 | SEQ ID NO: 105 | SEQ ID NO: 106 |
| CXCL12 | SEQ ID NO: 107 | SEQ ID NO: 108 | SEQ ID NO: 109 |
| NCR1 | SEQ ID NO: 110 | SEQ ID NO: 111 | SEQ ID NO: 112 |
| POU4F3 | SEQ ID NO: 113 | SEQ ID NO: 114 | SEQ ID NO: 115 |
| ZBTB16 | SEQ ID NO: 116 | SEQ ID NO: 117 | SEQ ID NO: 118 |

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09670546B2). An electronic copy of the "Sequence Listing" will also be available from the USPTO upon request and payment of the fee set forth in 37 CFR 1.19(b)(3).

The invention claimed is:

1. A method for determining the methylation state of at least one CpG dinucleotide in the region of the CDO1 gene as set forth in SEQ ID NO: 13 in a subject, comprising:
   obtaining from the subject a biological sample comprising breast cancer cell genomic DNA;
   treating the breast cancer cell genomic DNA isolated from the biological sample with at least one bisulfite reagent, or series of bisulfite reagents, that distinguishes between methylated and non-methylated CpG dinucleotides; and
   determining the methylation state of at least one CpG dinucleotide in the region of the CDO1 gene as set forth in SEQ ID NO: 13 in the biological sample from the subject, and detecting if methylation is present.

2. The method of claim 1, wherein determining the methylation state comprises: contacting the treated genomic DNA, or a fragment thereof, with an amplification enzyme and at least one primer comprising a contiguous sequence of at least 9 nucleotides that is complementary to, or hybridizes under moderately stringent or stringent conditions to a sequence selected from the group consisting of SEQ ID NO: 45, 46, 85 and 86, and complements thereof, wherein the treated genomic DNA or the fragment thereof is either amplified to produce at least one amplificate, or is not amplified; and determining, based on a presence, absence or amount of the amplificate, the methylation state or methylation level of at least one CpG dinucleotide of SEQ ID NO: 13, or an average, or a value reflecting an average methylation state or methylation level of a plurality of CpG dinucleotides of SEQ ID NO: 13.

3. The method of claim 1, wherein the bisulfite reagent, or series of bisulfite reagents, is selected from the group comprising of bisulfite, hydrogen sulfite, disulfite, and combinations thereof.

4. The method of claim 1, wherein the biological sample obtained from the subject is selected from the group comprising cell lines, histological slides, paraffin embedded tissues, biopsies, tissue embedded in paraffin, bodily fluids and all possible combinations thereof.

5. The method of claim 4, wherein the bodily fluid is nipple aspirate or blood.

* * * * *